United States Patent
Singer et al.

(10) Patent No.: US 11,207,213 B2
(45) Date of Patent: Dec. 28, 2021

(54) LACRIMAL PLUG INSERTER

(71) Applicants: Michael A. Singer, San Antonio, TX (US); Jeffrey Cheesman, Upper Saddle River, NJ (US); James Aman, Poinciana, FL (US)

(72) Inventors: Michael A. Singer, San Antonio, TX (US); Jeffrey Cheesman, Upper Saddle River, NJ (US); James Aman, Poinciana, FL (US)

( * ) Notice: Subject to any disclaimer, the term of this patent is extended or adjusted under 35 U.S.C. 154(b) by 197 days.

(21) Appl. No.: 16/360,541

(22) Filed: Mar. 21, 2019

(65) Prior Publication Data
US 2020/0297535 A1    Sep. 24, 2020

(51) Int. Cl.
A61F 9/007    (2006.01)
A61B 17/12    (2006.01)
A61M 29/00    (2006.01)

(52) U.S. Cl.
CPC .... *A61F 9/00772* (2013.01); *A61B 17/12099* (2013.01); *A61B 17/12159* (2013.01); *A61B 2017/1205* (2013.01); *A61M 29/00* (2013.01)

(58) Field of Classification Search
CPC .......... A61F 9/00772; A61B 17/12159; A61B 2017/1205; A61B 17/12109; A61B 17/30; A61B 2017/305; A61B 50/33; A61B 50/362; A61B 50/30; A61B 50/3001; A61B 17/12099; B25B 9/02; A61M 29/00
See application file for complete search history.

(56) References Cited

U.S. PATENT DOCUMENTS

| | | | | |
|---|---|---|---|---|
| 4,257,406 A * | 3/1981 | Schenk | .............. | A61B 17/0231 600/219 |
| 4,915,684 A * | 4/1990 | MacKeen | ............... | A61F 2/148 604/264 |
| 4,955,896 A * | 9/1990 | Freeman | ............ | A61B 17/0231 294/99.2 |
| 5,215,726 A * | 6/1993 | Kudla | ....................... | A61L 2/26 422/297 |
| 5,451,380 A * | 9/1995 | Zinnanti | ................... | A61L 2/26 206/370 |
| 5,630,821 A * | 5/1997 | Klaas | .................... | A61F 2/1664 606/107 |
| 5,921,990 A * | 7/1999 | Webb | ..................... | A61B 17/30 606/107 |
| 2011/0172675 A1* | 7/2011 | Danta | .................... | A61F 2/147 606/107 |

(Continued)

*Primary Examiner* — Darwin P Erezo
*Assistant Examiner* — Brigid K Byrd

(57) ABSTRACT

A medical instrument and method is described for facilitating lacrimal occlusion. The instrument has two arms for holding a plug being inserted through the punctum, each arm having a distal end and a proximal end. Attached to the proximal end of the arms is a dilator oriented in the opposite direction along the longitudinal axis of the instrument. The instrument is conveniently rotated in the hand of the practitioner to alternately present the functioning end of the instrument as either the distal end of the arms (for holding a plug) or the distal end of the dilator (for enlarging the punctum prior to attempting to inserting the plug). The instrument has a means for moving the two arms near to each other and away from each, and a means for holding the two arms near to each other without requiring closing pressure applied by the practitioner.

15 Claims, 15 Drawing Sheets

(56) References Cited

U.S. PATENT DOCUMENTS

2011/0196317 A1* 8/2011 Lust ................ A61B 50/30
                                                    604/290
2014/0364891 A1* 12/2014 Mendius ............ A61F 9/00772
                                                    606/191

* cited by examiner

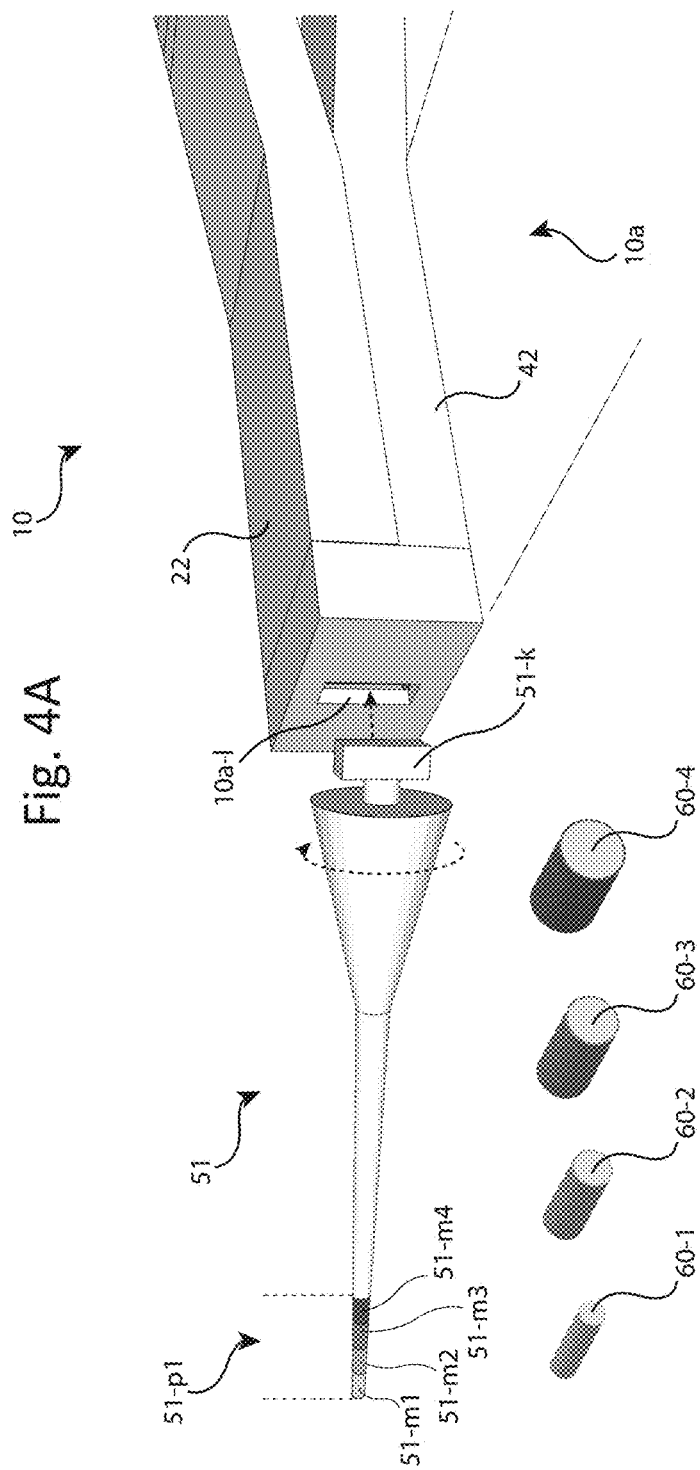
Fig. 4A
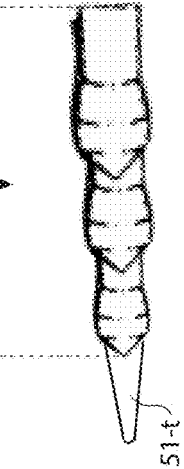
Fig. 4B
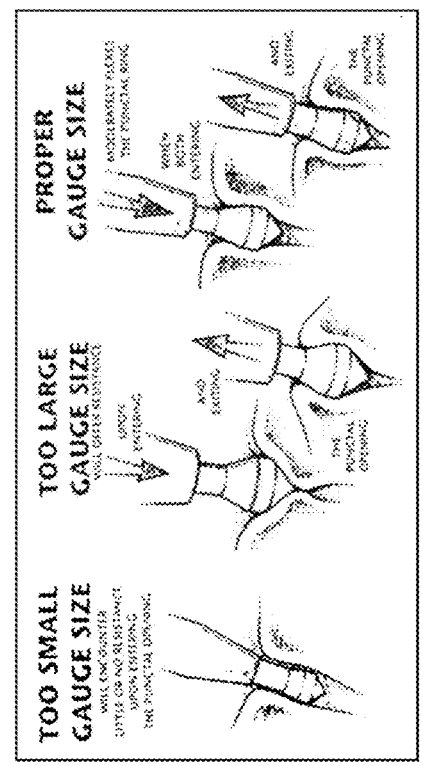
(reference art)

(Exemplary Reference Art Thumb Forceps)

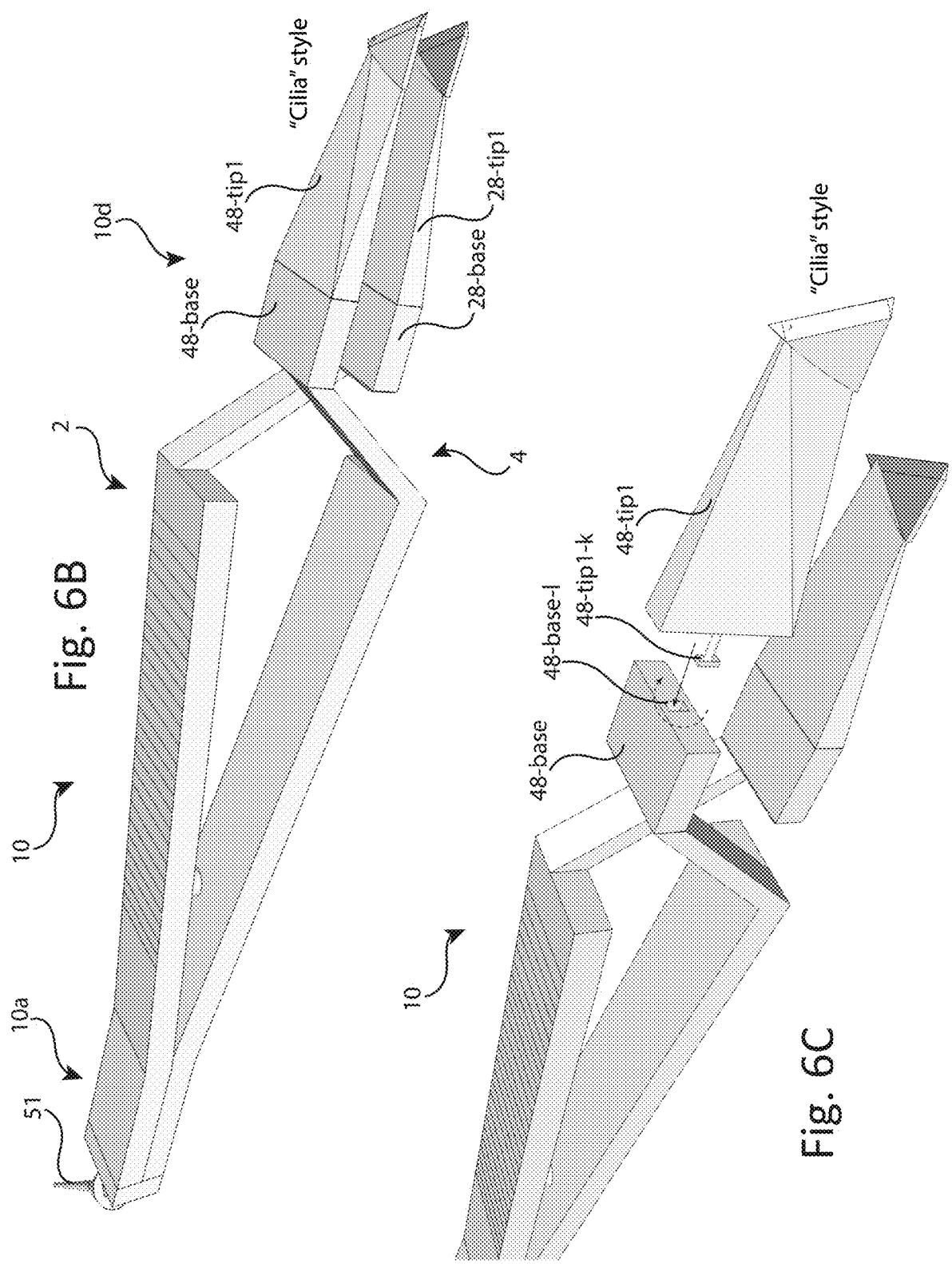

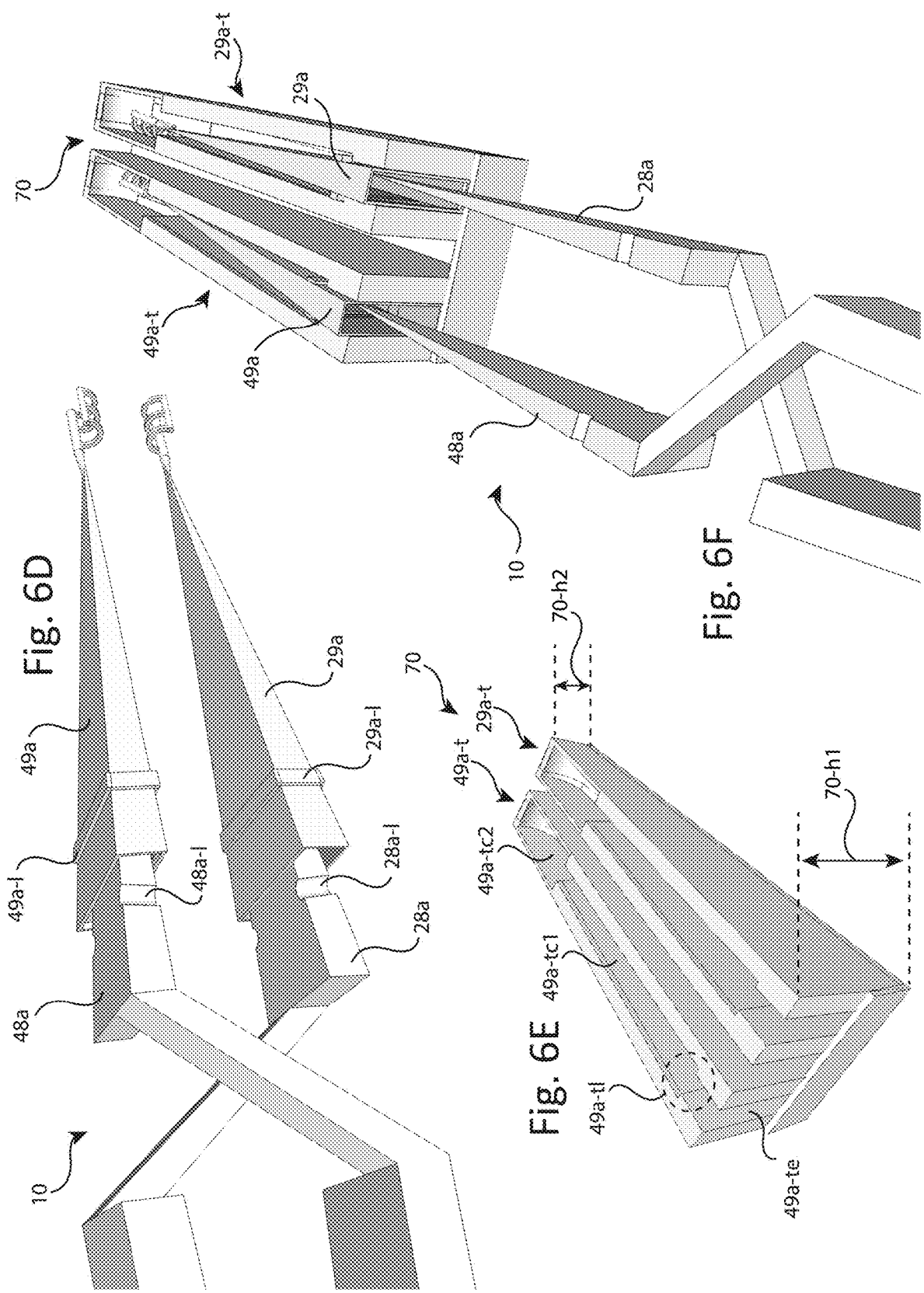

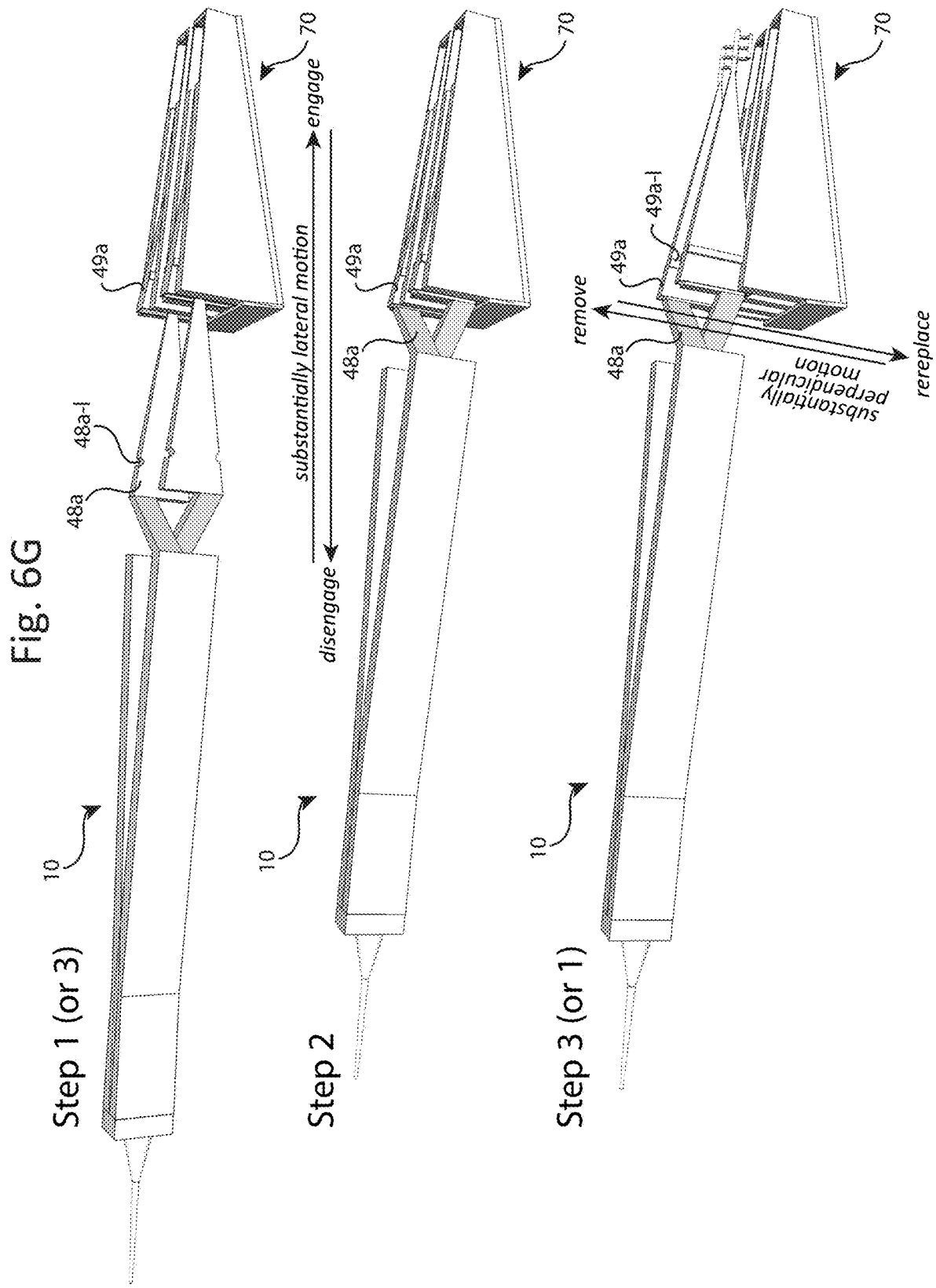

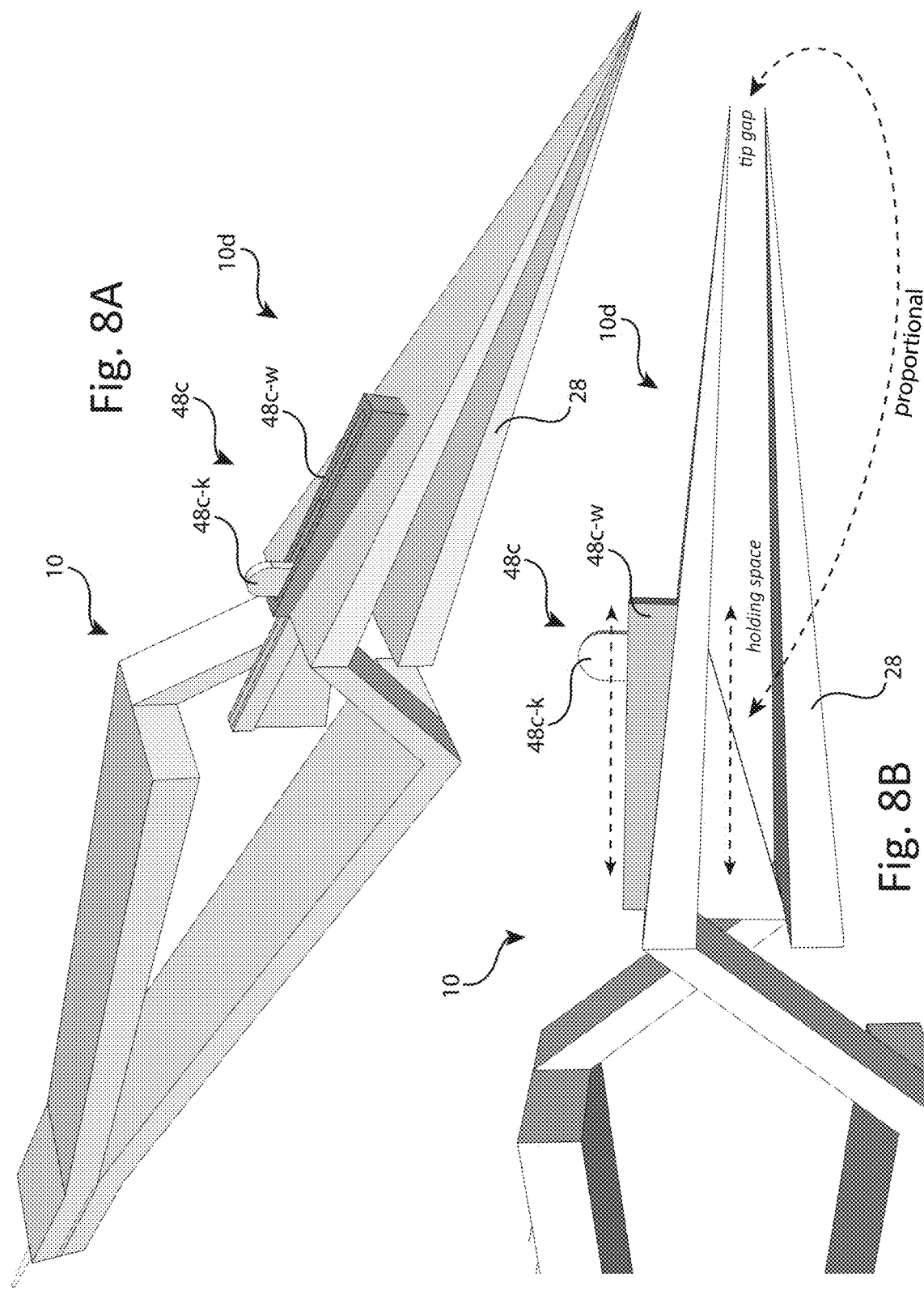

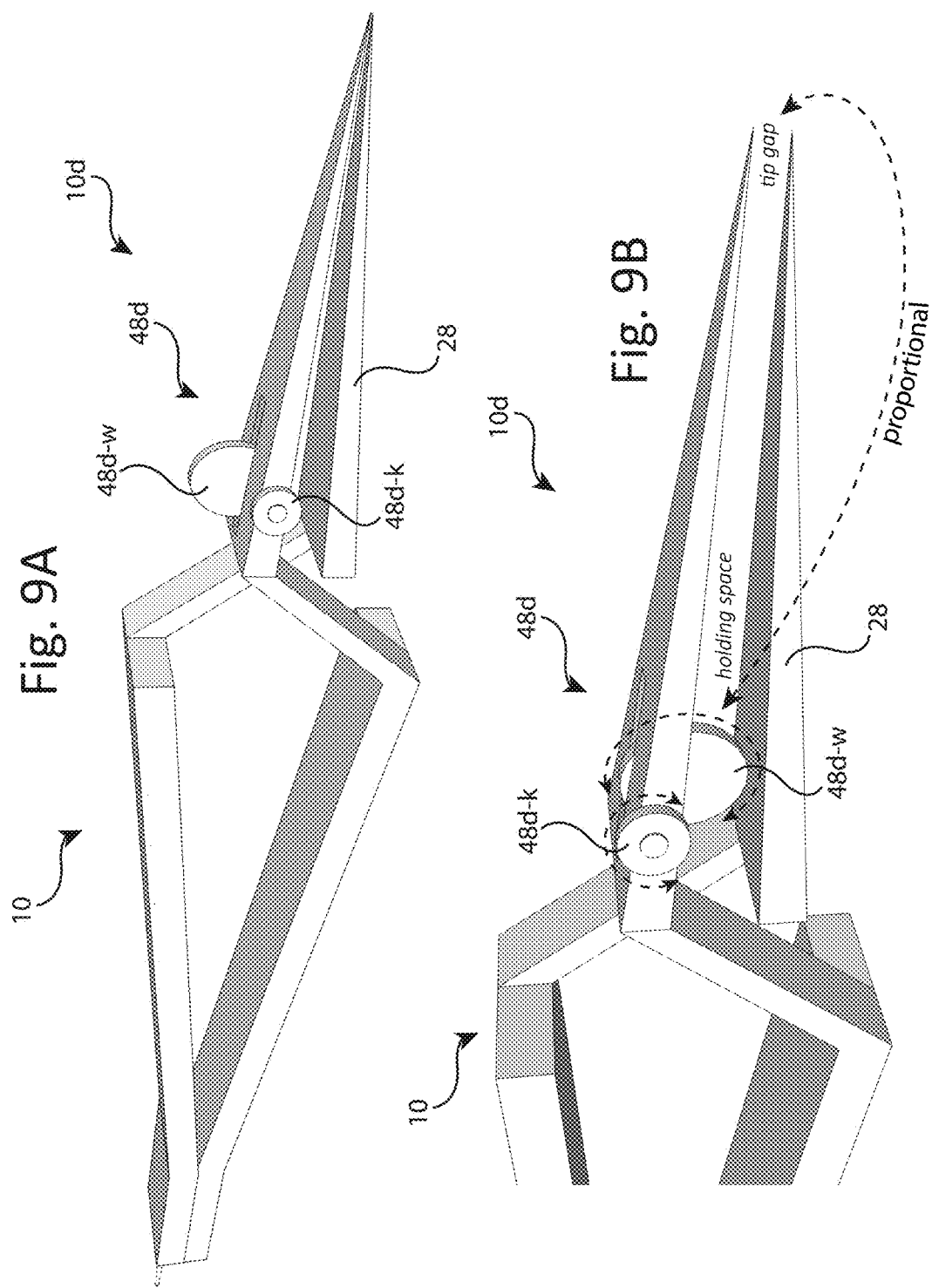

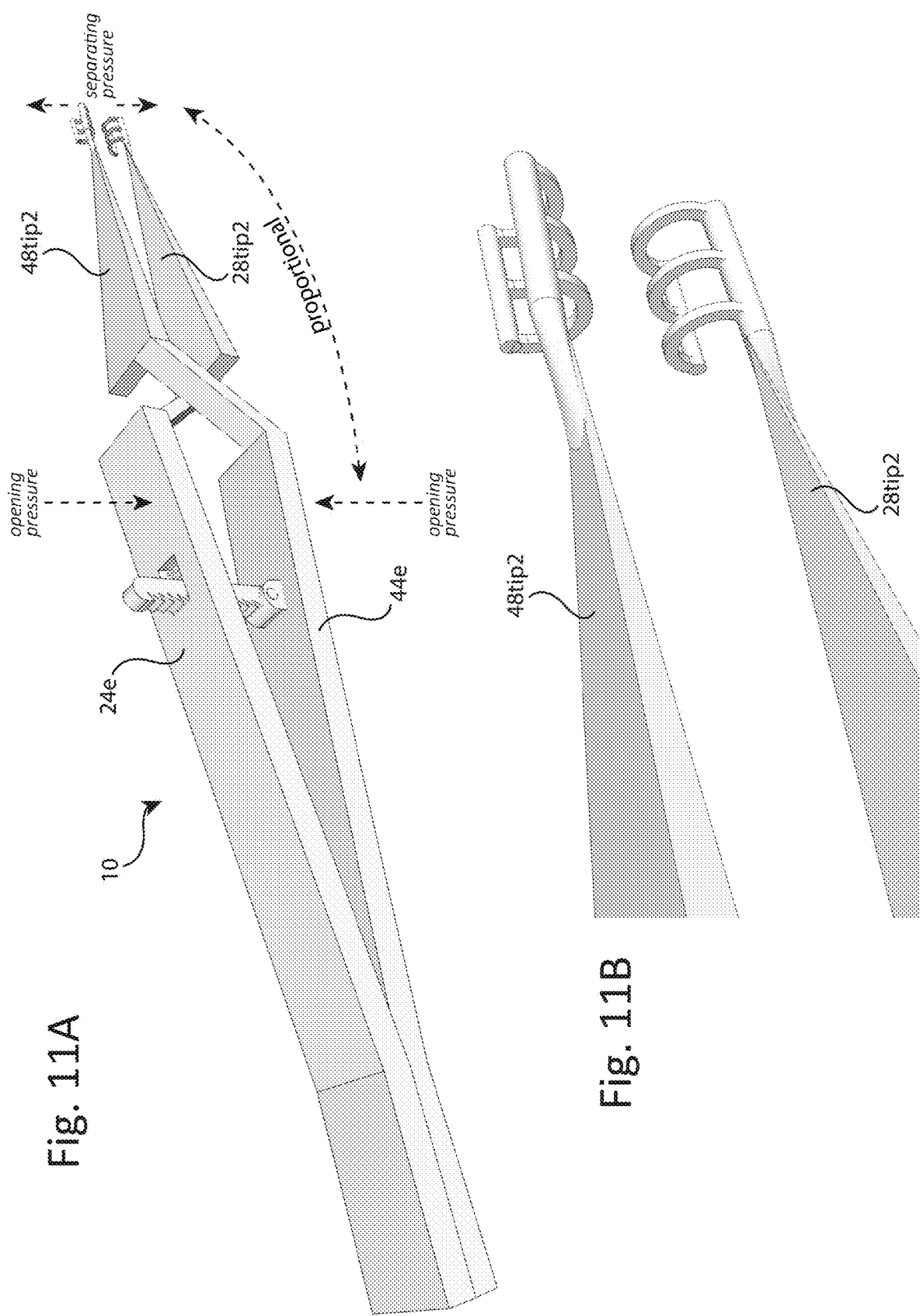

LACRIMAL PLUG INSERTER

FIELD OF THE INVENTION

The present invention relates, in general, to medical instruments and methods which facilitate the occlusion of the lacrimal duct by the insertion of either an intracanalicular or punctal plug. More particularly, it relates to a single lacrimal plug inserter that provides for both the functions of punctal dilation and plug engagement, insertion and disengagement, thereby providing more efficient and robust treatment methods.

BACKGROUND OF THE INVENTION

Dry eye is a common ailment for which there are different treatments including what is known in the art as lacrimal occlusion, where lacrimal refers to the lacrimal puncta which are small openings in the tear duct for draining tears secreted by the lacrimal gland and occlusion refers to the blocking of these ducts by the insertion of small plugs. An individual duct is referred to as a punctum, for which there are two basic types of occlusions; the first referred to as punctal occlusion and the second as intracanalicular occlusion. With punctal occlusion, a practitioner inserts into the punctum a punctal plug, usually including a flanged end, where the plug inserts into the punctum up to the flange but no further, thus leaving the flange exposed facilitating the extraction of the punctal plug if necessary, by allowing the plug to be pulled out from the punctum by the flange end. In the second type of intracanalicular occlusion, a practitioner inserts into and through the punctum an intracanalicular plug not including a flanged end, such that the intracanalicular plug can be pushed into the interior of the lacrimal (tear) duct referred to as the canaliculus.

In either type of occlusion, the plugs typically range in diameter between 0.4 mm and 0.8 mm and in price from $50 to over $250. In the most common type of lacrimal occlusion procedure having been practiced for over the last 40 plus years, three separate instruments are required, namely: 1) a punctal sizer, 2) a dilator, and 3) thumb forceps, all of which are well-known in the art. The procedure is typically performed by a practitioner without the aid of an assistant, and as such it is necessary that the practitioner switch their gaze between a concentration on the patient's punctum and a concentration on the selecting of instruments necessary for performing the occlusion, and more specifically switching between a dilator instrument and the thumb forceps during the more critical insertion portion of the process. The sizer instrument is used prior to the plug insertion process to help determine the size of the patient's punctum and therefore the diameter of an appropriate plug. The plug insertion process typically commences with the practitioner using the dilator tool to enlarge the orifice of the punctum after which the practitioner puts down the dilator instrument, picks up the thumb forceps, and then uses the thumb forceps to select the proper plug. After selecting the plug, the practitioner maintains a grasp of the plug by continuing to put a closing pressure on the thumb forceps, while then at the same time moving the plug to the punctum and then inserting the plug into the punctum. Once successfully inserted, the practitioner releases the applied closing pressure on the thumb forceps disengaging the plug that is partially inserted into the punctum. After releasing, the practitioner typically uses the distal end of the thumb forceps to further push the plug into the punctum as required by the type of plug. For a single patient, it is often necessary for the practitioner to insert multiple plugs, thus increasing the overall duration and cost of the procedure.

In this typical lacrimal occlusion process, there are several drawbacks including: 1) the plugs are small and somewhat soft (based upon their material composition, for example being collagen for temporary plugs or silicone for longer lasting plugs), where the combination of size and softness increases the dexterity required of the practitioner to apply the sufficient closing force for grasping the plug without excessive force that could damage the plug; 2) while applying the sufficient closing force and simultaneously moving the plug towards and into the punctum, it is not uncommon to drop the plug, where the loss of plugs is expensive, increases the mental stress of both the practitioner and the patient as the entire process duration is increased, and 3) when attempting to insert the plug, it is not uncommon that the practitioner determines that the punctum requires further dilation, thus requiring that the practitioner first disengage the plug by releasing the closing pressure on the thumb forceps, put down the forceps, pick up the dilator instrument, dilate the punctum, put down the dilator instrument, pick up the forceps, reengage the plug and attempt to again insert the plug, the combination of steps of which both add mental stress to the practitioner and patient, increase the duration of the process, increase the likelihood of dropping the plug, and distract the practitioner as they switch their gaze away from the patient's punctum.

BRIEF SUMMARY OF THE INVENTION

The present invention is a new medical instrument that combines the functions of bulldog forceps in combination with a dilator, thus providing a single instrument replacing the traditional two instruments including a separate dilator and separate thumb forceps. Unlike the thumb forceps which require a continuous closing pressure to be applied by the practitioner in order to maintain engagement of a plug, bulldog forceps only require an opening pressure (which is then relaxed) to engage the plug and an opening pressure to then disengage the plug (after insertion into the punctum). After applying opening pressure to separate the distal ends of the bulldog forceps in the process of surrounding the plug for engagement by the distal ends, the practitioner releases the opening pressure (or inversely stated applies closing pressure) that allows the distal ends to converge and engage the plug. Once so engaged, the positive pressure inherent between the distal ends of the bulldog forceps maintains the grasp of the plug without requiring any additional pressure from the practitioner (e.g. closing pressure if using thumb forceps). This removal by the present invention of the need for the practitioner to maintain an additional pressure offers many benefits to be described herein.

The presently described medical instrument also includes a dilator on the end of the instrument opposite to the distal end of the bulldog forceps (used for engaging a plug), where the distal end of the combined instrument is the functioning end of the instrument and always closest to the patient's punctum for the purposes of inserting or adjusting a plug. Given this two-in-one instrument, with a simple rotation of the instrument, the dilator that was proximal becomes distal and therefore also the functioning end. Conversely, with a second rotation of the instrument, the bulldog forceps distal ends become the distal and functioning end of the instrument. Given this convenient arrangement of not requiring additional pressure applied by the practitioner and including a dilator with the instrument easily accessed by a simple rotation of the instrument, it is now possible for the practitioner to: 1) be able to make the more delicate hand movements required for efficiently inserting the plug because the only physical hand exertion is to handle and move the instrument (and not also to additionally keep the distal ends of the instrument closed and engaging the plug as with thumb forceps), 2) be less concerned with dropping or damaging plugs as with the use of thumb forceps since the bulldog forceps maintain the appropriate continuous closing pressure without further concentration or effort from the practitioner, and 3) be able to switch from attempting to insert the plug to further dilating the punctum, and then back to attempting to insert the plug using a single tool simply rotated in the practitioner's hand, where then the practitioner is not required to divert their gaze from the patient's punctum thus improving the process and minimizing the process duration.

The present invention provides for further adaptations such that the two-in-one instrument becomes a three-in-one instrument, wherein the traditional function provided by a separate punctal-sizer is incorporated into the instrument's dilator, thus becoming a sizer-dilator. Hence, whereas a traditional lacrimal occlusion procedure requires three instruments including a punctal sizer, a dilator, and thumb forceps, the further adapted present invention provides each of these functions in a single convenient tool, thus saving valuable processes time for the practitioner, where this reduction in process time at least reduces the mental stress on the patient.

Other adaptations are provided for allowing the herein taught medical instrument to support a multiplicity of detachable end tips or end tip sleeves for engaging at least the punctal plugs, or a multiplicity of detachable dilators or detachable sizer-dilators for dilating the punctum and sizing the punctum. Using these further adaptations for detachable proximal or distal ends, it is also shown that the instrument is useful for at least other medical procedures such as trichiasis using a cilia style end tip and is also anticipated to be useful for other non-medical processes. With respect to the detachable end tip sleeves, the present invention teaches a new rack comprising one or more boxes, each box comprising two trays, each tray for holding a sleeve for use with a distal end of the instrument. In combination with the herein taught medical instrument, the rack, box and tray solution provides a convenient way for the practitioner to quickly select, replace or switch between a number of different end tips using only a single hand, thus further facilitating the optimization of at least medical procedures such as lacrimal occlusion.

And finally, the herein taught bull-dog mechanism is further adapted with various mechanical clamp-limiting means such that the practitioner can decrease the maximum clamping pressure the instrument will inherently provide, offering advantages in situations such as where the grasped material is of a softer composition for which the inherent closing pressure of the instrument is ideally limited to avoid possible damage to the material. At least one variation of the herein taught clamp-limiting mechanisms is shown to conveniently allow the practitioner to use the end tips in a separation function as opposed to a grasping function, for example to provide tissue separation and holding during a medical procedure such that the practitioner can then have access to the patient through the gap opened in the tissue.

As will be discussed with greater detail herein, the present invention therefore offers both a new lacrimal plug inserter with distinct advantages over traditional instruments and offers a new process that is significantly more efficient in terms of at least time duration (by minimizing practitioner movements) and average cost (by minimizing the dropping and loss of plugs and minimizing total procedure time.) Other objects and advantages are detailed forthwith in the remainder of the specification while still other objects and advantages will be obvious to those skilled in the art of lacrimal occlusion, trichiasis and other medical procedures.

BRIEF DESCRIPTION OF THE SEVERAL VIEWS OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 4A is a perspective drawing of medical instrument 10 where base 10a has been further adapted to accept a detachable dilator 50 (not depicted) or a sizer-dilator 51 (depicted). Sizer-dilator 51 provides both the dilator function of dilator 50 along with the sizer function traditionally provided by a separate punctal-sizer instrument, thereby allowing further adapted instrument 10 to provide all three traditional lacrimal occlusion functions of: 1) sizing the punctum; 2) dilating the punctum, and 3) inserting a plug into the punctum in a single convenient tool. Sizer-dilator 51 further includes various markings 51-$m1$, 51-$m2$, 51-$m3$ and 51-$m4$ covering the sizer profile 51-$p1$, where the various markings are usable for determining the appropriate plug size for selecting between plugs such as 60-1, 60-2, 60-3 and 60-4 of at least differing diameters.

FIG. 4B shows a reference art drawing illustrating the use of three different dimensioned punctal sizers to best determine the size of a patient's punctum. Also depicted in an alternative sizer profile 51-$p2$ for use with sizer-dilator 51, where alternative profile 51-$p2$ is based upon the combination of at least two of the reference art punctal sizer shapes, and where the profile 51-$p2$ preferably includes an optional dilator tip 51-$t$.

FIG. 6B is a perspective drawing of medical instrument 10 where holding surface 10d has been further adapted to comprise bases 48-base and 28-base for accepting a detachable distal end tip 48-*tip*1 and 28-*tip*1, respectively, where for example tips 48-*tip*1 and 28-*tip*1 are in the form of cilia style distal ends used for trichiasis, or alternatively of any shapes herein described or otherwise known in the reference art such as depicted in FIG. 6A.

FIG. 6C is a second view of the perspective drawing of medical instrument 10 further adapted to accept a detachable distal end tip 48-*tip*1 as shown in FIG. 6B, where the present figure depicts the detachable distal end 48-*tip*1 including key 48-*tip*1-*k* in a detached and orthogonal rotation prior to insertion into lock 48-*base-l* of distal end base 48-*base*.

FIG. 6D is a perspective drawing of the distal end of instrument 10, where distal end 48a and 28a have been further adapted to include latches 48a-*l* and 28a-*l*, respectively, for securing tip sleeves 49a and 29a, respectively, and where sleeves 49a and 29a further include interior latches (not depicted) for engaging latches 48a-*l* and 28a-*l* and exterior latches 49a-*l* and 29a-*l* for engaging a tray (see FIG. 6E).

FIG. 6E is a perspective drawing of sleeve box 70, comprising sleeve trays 49a-*t* and 29a-*t* for receiving, holding and discharging any of sleeves 49a and 29a, respectively. Each tray 49a-*t* and 29a-*t* such as 49a-*t* preferably further comprises a first tray cavity 49a-*tc*1 for holding the non-tip portion of a sleeve such as 49a, a second tray cavity 49a-*tc*2 for holding the tip portion of a sleeve such as 49a, an interior latch 49a-*tl* for impeding the lateral exit motion of a sleeve such as 49a and a lateral tray entrance 49a-*te* for receiving a distal end of instrument 10 such as 48a being inserted into a sleeve such as 49a held within tray 29a-*t*.

FIG. 6F is a perspective view of instrument 10 further adapted as described in FIG. 6D to comprise distal ends 48a and 28a partially inserted into sleeves 49a and 29a, respectively, where sleeves 49a and 29a are being held within trays 49a-*t* and 29a-*t*, respectively, comprising sleeve box 70 as described in FIG. 6E.

FIG. 6G is a side view diagram depicting three steps 1, 2 and 3 for first inserting (steps 1 and 2) via substantially a lateral motion distal ends such as 48a comprising latch 48a-*l* into sleeves such as 49a held within sleeve box 70, and second removing (step 3) via substantially a perpendicular motion sleeves such as 49a now secured via an interior latch (not depicted) to a distal end latch such as 48a-*l*, where in the perpendicular motion exterior latch 49a-*l* of sleeve 49a is substantially unimpeded by tray box 70. Whereas steps 1, 2 and 3 allow for the engagement and removal of sleeves such as 49a from the tray box 70 by instrument 10, a reversal of steps 1, 2 and 3 further allow for the replacement and disengagement of sleeves such as 49a from tray box 70 by instrument 10, wherein during the reversal of step 3 tray box 70 substantially impedes the removal of a sleeve such as 49a by catching exterior latch 49a-*l* during the extracting lateral motion, thereby disengaging a sleeve such as 49a from a distal end such as 48a.

FIGS. 8A and 8B depict the distal end 48 of presently taught medical instrument 10 that has been further adapted as distal end 48c comprising a sliding wedge type clamp-limiting means including knob 48c-*k* for pushing forwards and backwards by the practitioner, where pushing the knob 48c-*k* causes wedge 48b-*w* to slide commensurately forwards or backwards into the holding space between distal ends 48c and 28, thereby proportionately effecting the tip gap and associated closing (positive) pressure of instrument 10.

FIGS. 9A and 9B depict the distal end 48 of presently taught medical instrument 10 that has been further adapted as distal end 48d comprising a rotating oblong wheel type clamp-limiting means including knob 48d-*k* for turning by the practitioner, where turning the knob 48d-*k* causes oblong wheel 48d-*w* to rotate commensurately into the holding space between distal ends 48d and 28, thereby proportionately effecting the tip gap and associated closing (positive) pressure of instrument 10.

FIGS. 11A and 11B depict the distal ends 28 and 48 of the further adapted medical instrument 10 including a rachet type clamp limiter as taught in relation to FIGS. 10A and 10B, to be further adapted as tissue separating style distal ends 28*t*-2 and 48*t*-2.

DETAILED DESCRIPTION OF THE INVENTION

Figure 1:
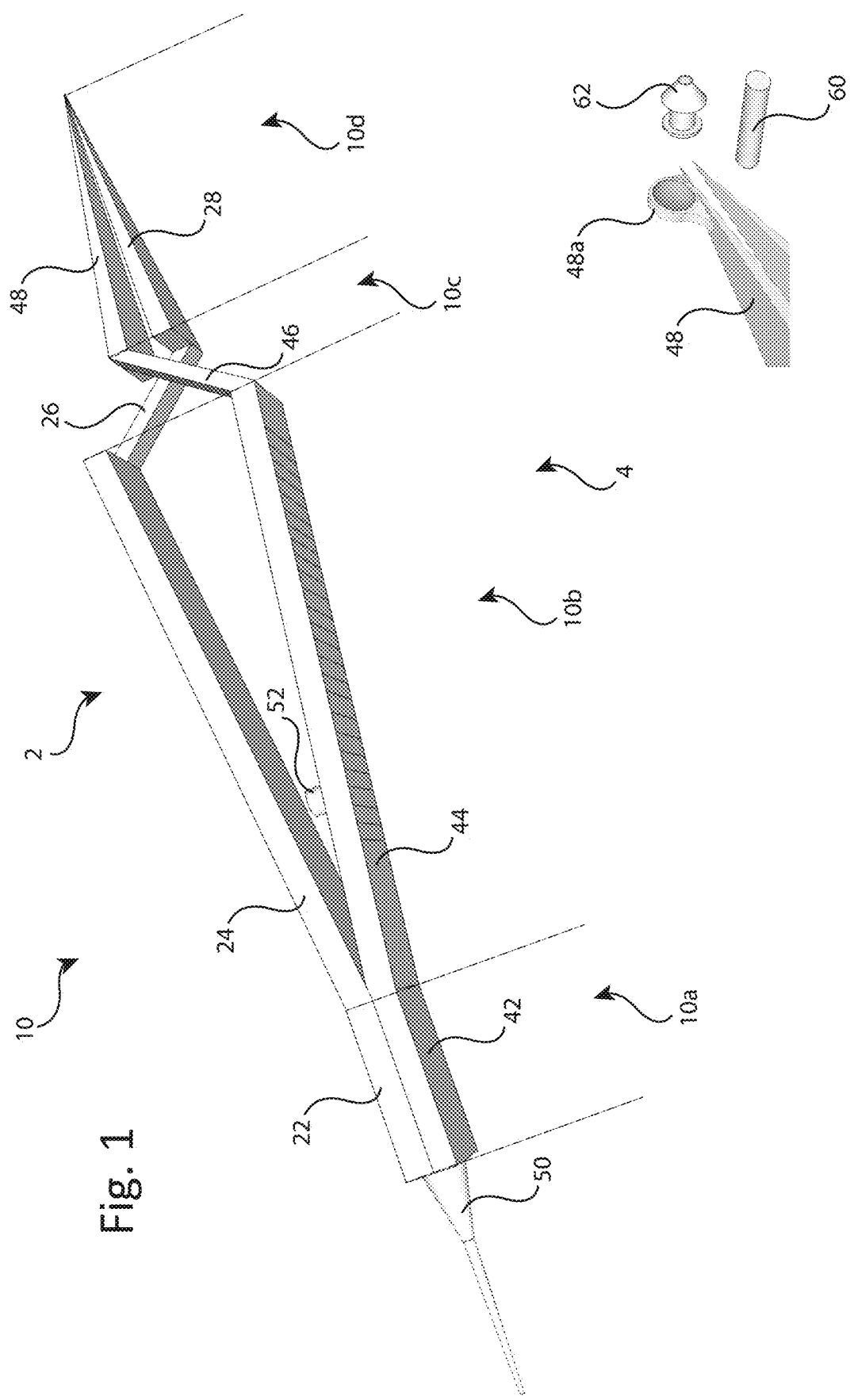
FIG. 1 is a perspective drawing of a novel medical instrument 10 comprising bull-dog style crossing arms 2 and 4 substantially for engaging, disengaging and otherwise manipulating a plug such as 60 or 62 used in a lacrimal occlusion medical procedure. Attached to arms 2 and 4 is dilator 50 such that tool 10 is easily manipulated by a practitioner between a dilator instrument and a plug grasping and insertion instrument.

Referring to FIG. 1, there is shown a perspective view of a first embodiment of medical instrument 10 that resembles a surgical (or "bulldog") forceps well-known in the medical art for the occlusion of blood vessels. Instrument 10 is about 60 mm long, although the length may vary, and comprises a first arm 2 and a second arm 4. First arm 2 is an elongated member made of a metal such as stainless steel or a rigid, medical grade plastic. Starting from the proximal end, the first arm 2 comprises a proximal portion 22, a wide portion 24 angled outwardly from the proximal portion, a narrow portion 26 angled inwardly from the wide portion 22, and a distal portion 28 angled outwardly from the narrow portion 26. The second arm 4 is like the first arm 2, comprising a proximal portion 42, a wide portion 44 angled outwardly from the proximal portion 42, a narrow portion 46 angled inwardly from the wide portion 44, and a distal portion 48 angled outwardly from the narrow portion 46. Proximal portions 22 and 42 are joined to one another, the combination of which form the base 10a. Wide portions 22 and 42 are detached from one another, the combination of which form a grasping surface 10b whereupon a practitioner preferably maintains hold of and operates instrument 10. It is preferred that at least the outer grasping surfaces of wide portions 24 and 44 include surface changes for increasing grip, such as a series of etched groves as depicted in the present figure with respect to portion 44. Narrow portions 26 and 46 are detached from one another, the combination of which form the inflection point 10c. Distal portions 28 and 48 are detached from one another and movable such that in a normal resting state portions 28 and 48 are touching while in an opening state portions 28 and 48 are separated by some distance, where the combination of distal portions 28 and 48 form the holding surface 10d for engaging and disengaging a plug such as 60 or 62. The present invention anticipates that at least the touching (and facing) surfaces of distal portions 28 and 48 can be any of smooth, rough, serrated or even hollowed shaped to best grasp a particular plug such as 60 or 62, and that preferably the combined closed tip ends of portions 28 and 48 form a sharp point, but can also form a blunt point.

Still referring to FIG. 1, as will be well understood by those familiar with the treatment of dry eye using lacrimal (or punctal) occlusion, there are many types of plugs for use in this procedure including for example intracanalicular plugs such as 60 without a flange and punctal plug 62 including a flange, where such plugs 60 and 62 come in various sizes, shapes and material compositions.

As will be understood by those familiar with bulldog forceps, a practitioner applies three distinct types of pressure to properly operate the instrument 10, including what is herein referred to as a handling pressure, an opening pressure and a closing pressure (where a closing pressure is actually the relaxing of the opening pressure). Using handling pressure, the practitioner is able to pick up, move about and put down the instrument 10 without causing any relative changes in the distance between the distal ends 28 and 48 of holding surface 10d. Hence, if the distal ends 28 and 48 are not already engaging a plug such as 60 or 62, then the ends 28 and 48 are touching and remain touching given only handling pressure. If the distal ends 28 and 48 are already engaging a plug such as 60 or 62, then the ends 28 and 48 are substantially separated by some distance as dictated by the size, shape and material composition of the plug 60 or 62 and the location in which the plug was engaged, and this separation distance remains substantially unchanged given only handling pressure. It is important to see that once a plug such as 60 or 62 is engaged by the practitioner using the holding surface 10d of instrument 10, there is only a minimum handling pressure required by the practitioner to then move about the plug 60 or 62 as is necessary for preforming the lacrimal occlusion procedure, where this minimum handling pressure does not further include any of opening or closing pressure.

Still referring to FIG. 1, in a typical use case, prior to a plug being engaged, a practitioner grasps instrument 10 for example placing their thumb somewhere on the wide portion 24 and their pointer finger somewhere on the wide portion 44, essentially encompassing grasping surface 10b. While in this plug-unengaged state of instrument 10, distal portion 28 is in contact with distal portion 48. When the practitioner the presses their grasping thumb and pointer finger's together to apply an opening pressure, wide portions 24 and 44 are brought together, and due to the crossing arrangement of narrow portions 26 and 46 forming inflection point 10c, distal portions 28 and 48 are thereby separated and no longer in contact. In a normal operation, while applying this opening pressure, the practitioner moves the distal ends 28 and 48 to surround some portion of a plug such as 60 or 62 and then applies a closing pressure by relaxing the opening pressure, thus causing distal ends 28 and 48 to engage the plug in some selected location. The practitioner is then free to move the plug such as 60 or 62 about as necessary without the additional strain of maintaining a closing pressure to secure the engaged plug, which is required when using the traditional thumb forceps for engaging a plug such as 60 or 62.

Still referring to FIG. 1, there is also shown separator 52 located preferably along an inside edge of either wide portion 44 (as depicted) or wide portion 24 (not depicted). The function of separator 52 is to limit the minimum separation distance between wide portions 24 and 44 as caused by the application of opening pressure by the practitioner. This limit is set to both allow sufficient separation distances between distal ends 28 and 48 to be achieved for engaging and disengaging plugs such as 60 and 62 while also disallowing a maximum opening pressure that might for example cause wide portions 24 and 48 to come into contact causing harmful strain on arms 2 and 4 or even breaking instrument 10. As will be obvious to those skilled in the art of instrumentation manufacturing, there are many possible locations for placing separator 52, and many shapes and sizes for separator 52, and even other means for accomplishing the same function. It is even possible to use multiple separators 52, for example each aligned to oppose each other thus essentially equally splitting the minimum limit. What is important to see is that preferably, but not necessarily, some adaptation is added to instrument 10 to function as a means for limiting the minimum separation distance between wide portions 24 and 44 as caused by the application of opening pressure by the practitioner.

Still referring to FIG. 1, instrument 10 preferably also includes a dilator 50 attached to the base 10a of instrument 10 such that the dilator 50 points in the opposite direction of distal portions 28 and 48, thus providing instrument 10 with a dual-function of both dilating a patient's punctum with dilator 50 and engaging and disengaging a plug such as 60 or 62 with distal portions 28 and 48. The preferred shape of the dilator 50 is wider at the point of attachment to the base 10a, tapering off to form a point at the functioning end. In the preferred arrangement, dilator 50 is permanently attached to the base 10a. However, it is further anticipated that the dilator 50 can be detachable from the base 10a, for example where dilator 50 includes a threaded screw (or "key and lock", see upcoming FIG. 4A) and therefor can be screwed into an appropriately sized threaded opening in the base 10a. Using this detachable dilator 50 alternate embodiment of instrument 10, it is then possible to allow instrument 10 to further adapt to different sized dilators 50 and even to further adapt to other types of tools for use in combination with the clamping arms 2 and 4. The present invention anticipates that the functioning tip end of dilator 50 can be sharp or blunt, or have various other shapes and designs commonly utilized within the ophthalmology industry, where for example the detachable dilator 50 can vary in any of these features.

And finally, in the lower right-hand corner of FIG. 1, juxtaposed with exemplary plugs 60 and 61 there is depicted an exemplary end tip adaptation referred to as plug receptacle 48a. In one possible operation of instrument 10, after the practitioner uses distal ends 48 and 28 (in any tip configuration, for example see upcoming FIG. 6) to first engage a plug, second partially insert the plug, and third disengage the plug, the practitioner then uses the plug receptacle 48a as a means for better manipulating the plug for further insertion into the punctum, where better manipulating includes receiving the end of the plug currently protruding from the punctum into the concavity of receptacle 48a, such that once received the practitioner is better able to guide and apply directional pressure upon the plug for insertion into the punctum.

As will be clear based upon a careful consideration of the purposes of plug receptacle 48a, especially to those familiar with medical instruments and the lacrimal occlusion procedure, there are many possible forms and arrangement for plug receptacle 48a and thus the present depiction should be considered as exemplary, rather than as a limitation of the present invention. For example, plug receptacle 48a as currently depicted with a concavity parallel to the grasping and therefore plug insertion axis, could alternately be rotated for example 90 degrees to be perpendicular with the direction of plug insertion. Additionally, and alternatively, the plug receptacle 48a could be a of different size, shape or attached location while still providing for the essential means of receiving the plug to improve the practitioner's control during the insertion process. And finally, with respect to variations of plug receptacle 48a, it is even possible that the receptacle 48a is divided into two left-right partitions, centered with respect to each other and located between the tips 48 and 28, where for example the "left half" of divided receptacle 48a (comprising essentially half of 48a) is comprised within the tip of distal end 48 and where essentially the remaining "right half" of 48a is comprised within the tip of distal end 28, such that after disengaging a plug and due to the inherent positive pressure of instrument 10 the two distal ends 48 and 28 are in contact and collectively form the receptible 48a by bringing the left and right halves of divided alternate receptacle 48a together between the tips for a similar usefulness of receiving and more easily guiding the a plug.

Figure 2:
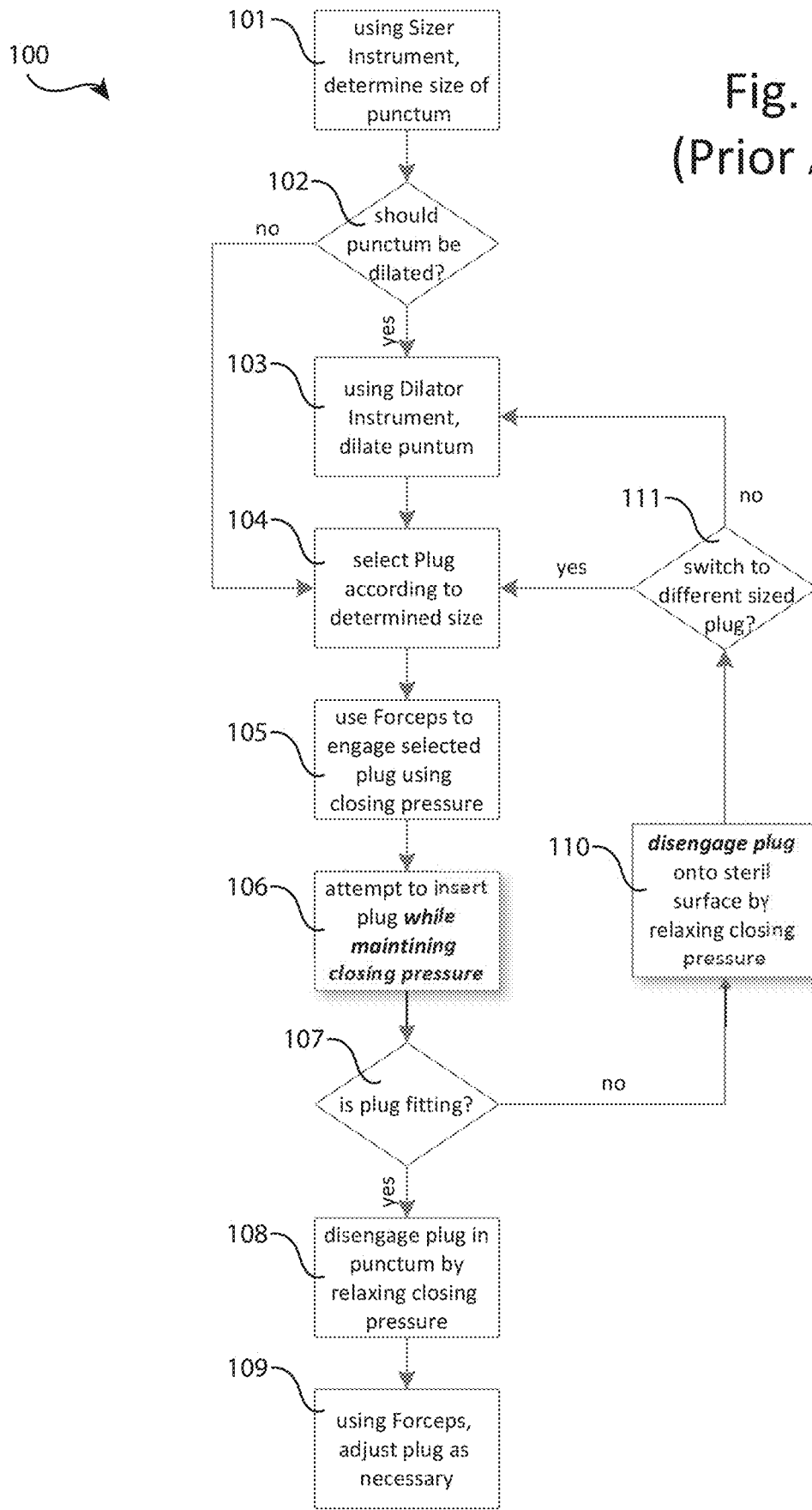
FIG. 2 is a flow chart describing the steps involved with a traditional lacrimal occlusion process 100 that relies upon the use of three distinct tools including a sizer instrument, a dilator instrument and a thumb forceps instrument.

Referring next to FIG. 2, there is shown a flow diagram describing the basic steps for performing the lacrimal occlusion process 100 as currently and commonly practiced in the art. First, it should be noted that the current process 100 requires three distinct tools, namely: 1) a first sizer instrument for measuring the size of the patient's punctum into which a plug such as 60 or 62 is to be inserted, sometimes referred to as a punctal sizing gauge; 2) a second dilator instrument for inserting into the punctum to cause the opening to enlarge in preparation for receiving the plug, and 3) a third thumb forceps instrument for grasping and holding a plug such as 60 or 62 using a continuous closing pressure while attempting to insert the plug into the punctum.

Still referring to FIG. 2, in a first step 101, the practitioner uses one or more sizer instruments to probe and estimate the size of the patient's punctum, for example determining that the punctum size is 0.6 mm. In step 102, the practitioner decides if the punctum should first be dilated prior to attempting to insert a plug such as 60 or 62. If the decision is "no," the practitioner proceeds to step 104, and otherwise if "yes" then performs step 103 using a separate dilator instrument to apply pressure on the punctum slightly enlarging its orifice. Next, in step 104 the practitioner selects an appropriate plug such as 60 or 62 based upon the chosen medical procedure (for example an intracanalicular plug such as 60 without a flange for inserting through the punctum into the interior of the lacrimal duct (canaliculus), and punctal plug 62 for partially inserting into the canaliculus such that the flange is still protruding from the puncta, all as is well known in the art). In step 105, the practitioner uses a traditional thumb forceps instrument that is in an open position in the resting state (i.e. without external closing pressure being applied by the practitioner), to first surround and then grasp the selected plug, where grasping means that the practitioner applies a closing pressure on the arms of the thumb forceps in order to cause the distal ends of the forceps' arms to close and engage the plug.

Continuing with step 106, the practitioner then attempts to insert plug such as 60 or 62 into the punctum. It is important to note the following difficulties with this step: 1) the step is performed around the patient's eye which is both uncomfortable for the patient and puts the patient at some risk, therefore the step duration is ideally limited; 2) both the punctum and the plug are small requiring precise movements from the practitioner; 3) the practitioner is required to maintain a sufficient closing pressure for continuing to secure the plug with the thumb forceps while at the same time moving their hand to direct the plug into the punctum, where this combination of exertion is delicate increasing the likelihood of either dropping the plug or having the plug slip in its initial position with respect to the grasping forceps (thus needing to be set down and repositioned delaying the total step time), and 4) the plugs such as 60 or 62 are easily dropped (for example by releasing closing pressure during step 106) or damaged (for example by applying too much closing pressure during step 106), which is costly as a typical plugs range in price from $50 to over $250 each.

Still referring to FIG. 2, at some point in step 106 the practitioner will decide as step 107 if the plug is fitting through the punctum. If "yes," this fitting results in at least a partial insertion of the plug through the punctum into the canaliculus such that the practitioner in step 108 is then able to release closing pressure disengaging the plug from the distal end of the thumb forceps to remain at least partially inserted through the punctum. In final step 109, the practitioner then typically uses the distal end of one of the forceps' arms to further push the plug into the canaliculus but still protruding from the punctum (e.g. if a punctal plug 62), or all the way into the canaliculus and not still protruding from the punctum (e.g. if an intracanalicular plug 60), where full insertion often requires the practitioner to switch from using the forceps to using the dilator instrument since the dilator has a single narrowed and elongated point that is ideal for pushing the plug deeper into the canaliculus, and where then this switching has the negative effects of both drawing the attention of the practitioner away from the patient's punctum and further increasing the duration of the process.

It should be noted that the distal end of one of the arms of the forceps is not an ideal tool for pushing the plug further into the punctum, for example as compared to a single ended tool such as a dilator instrument, where the pointed end of the dilator can be better used to push the plug. In a careful consideration, one of the problems with using the thumb forceps to further push the plug is that while the distal end of one arm is being used to push upon the plug, the distal end of the opposing arm is free and separated presenting itself closer to the patient's eye depending upon the motions chosen by the practitioner. In any case, it is not ideal that the practitioner take their eyes off the plug or otherwise divert their attention during the continuous performance of steps 106 through 109, (during which for example the patient could blink or in some way cause the plug to dislodge and therefore requiring a restart with a new plug). Since the practitioner is required to maintain their focus on the plug and since the practitioner typically does not have an assistant to which they could hand the thumb forceps and request a different tool such as the dilator instrument, the practitioner is forced to continue the fitting in step 109 using the thumb forceps.

Referring still to FIG. 2, if the practitioner decides that the plug is not fitting, i.e. "no," in step 107, then rather than proceed to step 108 the process continues to step 110. In step 110, regardless of the reason that the plug such as 60 or 62 is not fitting, the practitioner is forced to disengage the plug from the thumb forceps to be set down preferably on a sterile surface. This disengagement is caused by the practitioner relaxing their continuous closing pressure being applied in step 106, thus resulting in opening pressure that causes the distal ends of the forceps to separate, thus dropping (i.e. disengaging) the plug. In step 111, the two main reasons why the decision of step 107 is "no" are: 1) a different sized plug is needed, or 2) the punctum orifice should be further expanded using a dilator. Both situations are common, but it is most often the case that the practitioner simply needs to further dilate the punctum (i.e. returning to step 103). As a careful consideration will show, since the practitioner must maintain a closing pressure on the plug using the thumb forceps, it is not possible to keep the plug engaged by the forceps before returning to step 103, this is even true if the forceps where further adapted to include an attached dilator. Hence again, if in step 107 the practitioner decides "no" that the plug is not fitting for any reason, it is always necessary to perform step 110, i.e. disengaging the plug from the thumb forceps where this step only further unfavorably delays the entire process and increases the risk of dropping or damaging the plug.

Figure 3:
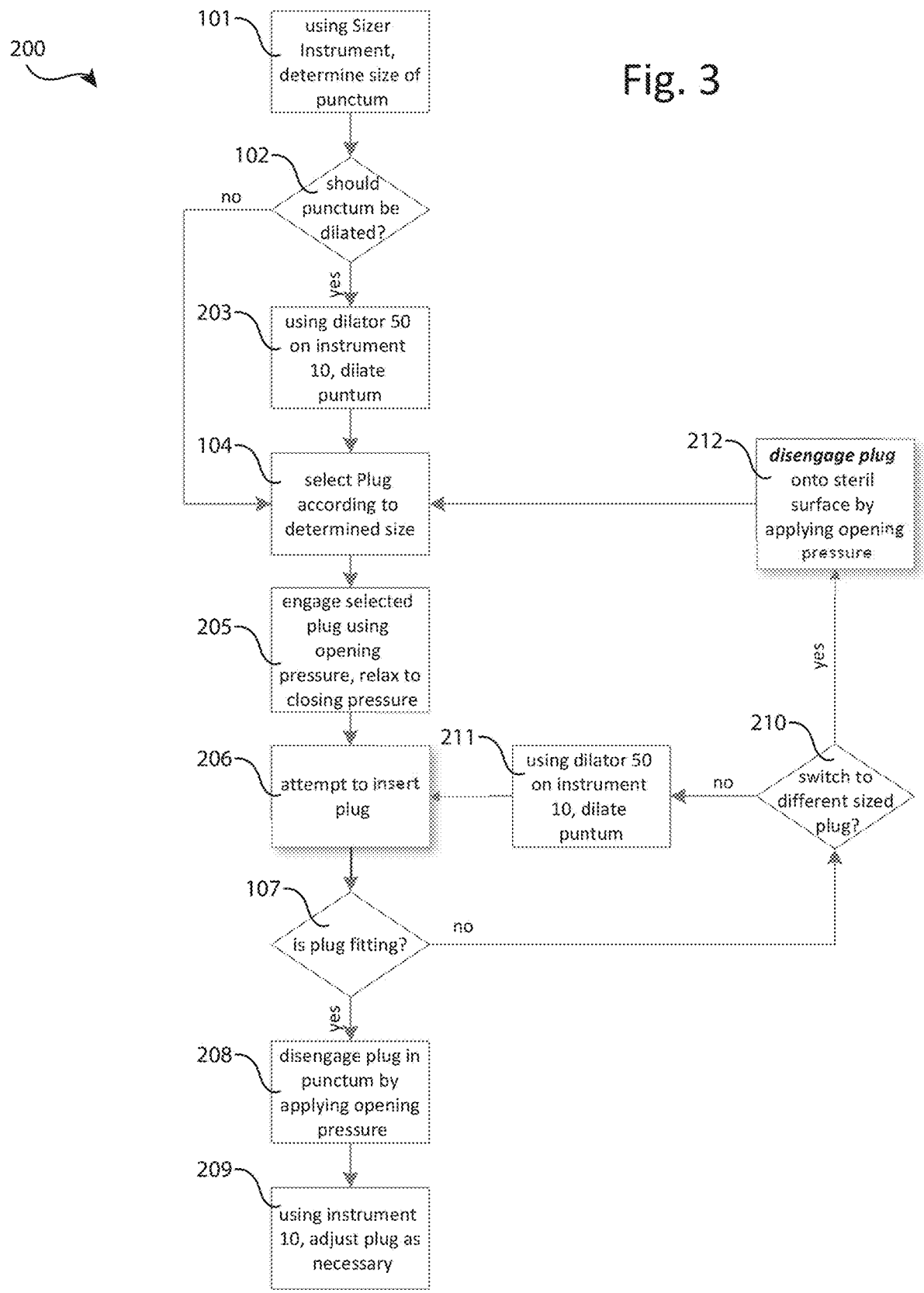
FIG. 3 is a flow chart describing the steps involved with the lacrimal occlusion process 200 according to the present invention that relies upon two distinct tools including a sizer instrument and the present medical instrument 10 as depicted in FIG. 1, where instrument 10 provides for both the functions of punctal dilation and plug engagement, insertion and disengagement.

Assuming the most common case that the reason the plug is not fitting is that the punctum needs further dilation, it will then be shown in upcoming FIG. 3 a distinct advantage of the presently described medical instrument 10. In this most common case, using the traditional thumb forceps, the practitioner must: 1) disengage the plug and set down the thumb forceps (step 110), 2) pick up the dilator tool and further dilate the punctum (step 103), 3) set down the dilator tool and then re-select (at least requiring a refocusing of vision and attention) the plug for reinsertion (step 104), and then must 4) pick up the thumb forceps and reengage the selected plug. As will be shown with respect to upcoming FIG. 3, in the most common case of needing further dilation in response to steps 107 and 111, the present invention avoids: 1) step 110 of disengaging the plug followed by setting down the thumb forceps; 2) picking up a separate dilator tool to perform step 103 which draws the practitioner's gaze away from the patient's punctum (as opposed to flipping the medical instrument 10 in the practitioner's hand to present the dilator 50 as the functioning end of the instrument 10 while at the same time the practitioner continues to focus their gaze on the punctum); 3) setting down the separate dilator tool in order to pick up the thumb forceps to perform step 105 which draws the practitioner's gaze away from the punctum (as opposed to flipping the medical instrument 10 in practitioner's hands to present the distal ends 28 and 48 still engaging the plug as the functioning end of the instrument 10 while at the same time the practitioner continues to focus their gaze on the punctum), and 4) re-focusing on (i.e. selecting) the plug in step 105 and applying closing pressure on the thumb forceps to re-engage the plug which further draws the practitioner's gaze away from the punctum and delays the medical procedure (again, as opposed to flipping the medical instrument 10 in practitioner's hands to present the distal ends 28 and 48 still engaging the plug as the functioning end of the instrument 10 while at the same time the practitioner continues to focus their gaze on the punctum).

Still referring to FIG. 2 and the process of the prior art implemented using thumb forceps, at least steps 106 and 110 are especially problematic, and then also steps 103, 105 and 109 are non-ideal.

Referring next to FIG. 3, there is shown a flow diagram describing the basic steps for performing the lacrimal occlusion process 200 using the preferred and herein taught medical instrument 10. As with traditional process 100, in the preferred process 200 steps 101 and 102 are first performed by the practitioner for determining both the size of the patient's punctum (step 101) and deciding if the punctum should be dilated (step 102). If it is decided that the punctum does not require dilation, the practitioner then proceeds to step 104, which is the same as in process 100. If it is decided that the punctum does require dilation, then in step 203 the practitioner selects new medical instrument 10 (rather than a separate dilator) and orients the instrument 10 such that the dilator 50 end is the functioning end (i.e. currently pointing outward/away from the practitioner's hands and body for use on the patient). After picking up instrument 10, the practitioner dilates the patient's punctum using dilator 50 attached to instrument 10.

Still referring to FIG. 3, and now proceeding from step 203 to step 104, the practitioner then selects the appropriately sized plug such as 60 or 62 by scanning with their eyes to find the plug's location and to confirm the plug's type and size. Once located and confirmed in step 104 (that is substantially like step 104 in process 100), unlike step 105 in process 100, the practitioner performs a simplified step 205 in process 200. Specifically, since the practitioner is already holding instrument 10 (for using the dilator 50 in step 203), the practitioner then continues to maintain a grasp of instrument 10 rotating the instrument 10 such that the distal ends 28 and 48 are now the functioning end, after which the practitioner applies opening pressure to arms 2 and 4 of instrument 10 to separate distal ends 28 and 48 for surrounding and engaging the selected plug such as 60 or 62, where a careful consideration will show that after surrounding the plug the practitioner relaxes the opening pressure (thus applying closing pressure) that allows the distal ends 28 and 48 to engage the plug using the positive pressure inherent in the proper construction of instrument 10 (that is typically a spring tension as implied in the depiction of instrument 10 in FIG. 1, although many solutions are available as will be well known to those familiar with bulldog forceps).

Proceeding now to step 206, there is another substantial difference to be considered between the present invention and the prior art. In step 206, as opposed to process 100 step 106, the practitioner does not need to apply any closing pressure because this closing pressure is being provided by the instrument 10. Instead, the practitioner is free to use handling pressure alone to manipulate the instrument 10 and thereby the plug such as 60 or 62, guiding and directing it into the patient's punctum. As will be clear upon a careful consideration, in process 100 the physical effort of maintaining a sufficient but not excessive closing pressure on the plug using thumb forceps, while then also moving the hand to adjust the plug's location, is significantly more complex than the presently described step 206 and often exacerbates the unwanted shaking of the practitioner's hand which further places the patient at risk. As prior discussed, this present instrument 10 and process 200 have many benefits including: 1) reducing any likelihood that the plug is dropped, where dropped plugs cost significant money; 2) decreasing the muscle movement complexity required by the practitioner thus reducing mental stress and physical handing shaking; 3) enhancing the efficiency of the procedure as the practitioner is no longer concerned with dropping the plug and can move the instrument 10 with greater ease, where the increased efficiency results in a minimum of process duration for the patient thus reducing the patient's mental stress, and 4) decreasing the likelihood of inadvertently touching and possibly hurting the patient's eye due to the need to manage a greater volume of space created by the separated distal ends of normal resting state thumb forceps as compared to the lesser volume of space created by the touching distal ends 28 and 48 of normal resting state instrument 10 (see step 209). Other benefits will be clear to those familiar with the lacrimal occlusion procedure.

Still referring to FIG. 3, after achieving at least partial insertion of the plug such as 60 or 62 into the patient's punctum, like process 100, the practitioner decides in step 107 if the plug is fitting. If the answer is "yes," then in step 208 the practitioner applies opening pressure to separate the distal ends 28 and 48 of instrument 10 in order to disengage the plug. After disengaging the plug, the practitioner then relaxes the opening pressure (thus applying closing pressure) to the cause the distal ends 28 and 48 to return to a resting, disengaging and touching position. The careful reader will note the advantages that distal ends 28 and 48 of instrument 10 are touching (thus taking up less volume) as opposed to the distal ends of a traditional thumb forceps that are separated while in the resting and disengaged state (thus taking up more volume). As prior mentioned, the total volume encompassed by the touching distal ends 28 and 48 of instrument 10 are less than the total volume encompassed by the distal ends of traditional thumb forceps, thus creating a safer tool for use near the patient's eye and also making it easier for the practitioner to adjust the instrument 10 for prodding the plug, pushing it further into the punctum as dictated by the chosen medical procedure.

If the answer to step 107 (is the plug fitting) is "no," then unlike process 100 the practitioner is not required to always disengage the plug but rather may first consider in step 210 if a different sized plug is necessary. If a different plug is necessary, then the practitioner completes step 212 and disengages the plug by applying opening pressure. Once disengaged, the practitioner is then free to proceed to step 104 to repeat process 200 from the point of selecting a plug. As those familiar with lacrimal occlusion procedures will understand, it is more often the case that the answer to step 210 (is a different sized plug needed) is "no." In this case, the present invention offers another significant benefit in that the practitioner is not required to: 1) disengage the plug (process 100, step 110); 2) set down the thumb forceps, and 3) pick up the separate dilator instrument all prior to further dilating the patient's punctum (process 100, step 103). Furthermore, as a careful comparison of process 200 versus 100 will show, in process 100 after this second dilation (i.e. process 100, step 103) the practitioner then must proceed to step 104 through 105 before again attempting to insert the plug in process 100 step 106, whereas in process 200, after completing step 203 the practitioner is enabled to proceed directly to step 206 (i.e. skipping steps 104 and 205 in favor of simply rotating instrument 10 to present the distal ends 28 and 48 still engaging the plug as the functioning end of the instrument 10).

In summary of the present inventive step 211, the practitioner keeps the instrument 10 in their hands while rotating the instrument 10 such that the dilator 50 is the functioning end. Once this simple rotation is made, the practitioner is free to dilate the patient's punctum. After dilation, rather than having to then set down a separate dilator instrument and proceed to a process 100 step 104, 105, etc. using thumb forceps, the practitioner simply rotates the distal ends 28 and 48 (currently and still engaging the prior selected plug), such that the distal ends are the functioning end of instrument 10. Once rotated, the practitioner then proceeds to step 206 as prior described.

Referring now to both FIGS. 2 and 3, what is clear is that the new instrument 10 and process 200 offer significant advantages over traditional thumb forceps and a traditional thumb forceps-based process 100. The use of new instrument 10 and process 200 have many benefits including: 1) reducing any likelihood that a plug is dropped, where dropped plugs cost significant money; 2) decreasing the muscle movement complexity required by the practitioner thus reducing both mental stress and physical hand shaking; 3) enhancing the efficiency of the procedure as the practitioner is no longer concerned with dropping the plug and can move the instrument 10 with greater ease, where the increased efficiency results in a minimum of process time for the patient thus reducing the patient's mental stress; 4) avoiding the need to always disengage the plug, set down the thumb forceps, and pick up a separate dilator instrument if all that is required during the insertion process is a further dilation of the patient's punctum, where after dilation the present invention then also avoids needing to set down the separate dilator, pick up the thumb forceps, find and re-engage the plug prior to continuing the insertion step, the excessive combination of which distracts the practitioner's attention from the patient and increases the duration of the process and the patient's mental stress; 5) decreasing the likelihood of inadvertently touching and possibly hurting the patient's eye during adjustment step 209 due to the reduced volume of space taken up by the touching distal ends 28 and 48 of instrument 10 as compared to step 109 where the normally separated distal ends of the thumb forceps create an increased volume making their use as a prodding tool more difficult; and 6) providing the practitioner a single instrument 10 choice between means for prodding, pushing and adjusting the plug during step 209, where the choice is to use the touching distal ends 28 and 48 or to rotate instrument 10 and use the dilator 50, where the dilator 50 is especially useful for pushing a intracanalicular plug such as 60 deeper into the canaliculus especially as opposed to using separated thumb forceps distal ends. Other benefits will be clear to those familiar with the lacrimal occlusion procedure, for example, it is sometimes the case that after insertion the practitioner decides it is necessary to remove the plug such as 60 or 62, in which a careful consideration will show that it is far more efficient for the practitioner to remove the plug using instrument 10 if just prior to this the same plug was being pushed further into the punctum using a dilator therefore requiring a switch back from the dilator to a grasping tool (such as thumb forceps or the distal ends 28 and 48 of instrument 10).

Referring next to FIG. 4A, there is shown a perspective drawing of medical instrument 10 where base 10a has been further adapted to accept a detachable dilator 50 (not depicted) or a sizer-dilator 51 (depicted). Sizer-dilator 51 provides both the dilator function of dilator 50 along with the sizer function traditionally provided by a separate medical instrument. In particular, the distal end of sizer-dilator 51 includes a sizer profile 51-p1 that is preferably an elongated conical shape increasing continuously and smoothly in diameter starting at the distal tip proceeding at least part way towards the base of sizer-dilator 51, where the base of sizer-dilator 51 includes a mechanism for attaching to the base 10a of instrument 10. While those familiar with mechanical systems will recognize that many possible mechanisms for attaching a detachable sizer-dilator 51 or dilator 50 to base 10a are possible, for example a simple screw/screw hole combination, the preferred detachable sizer-dilator 51 (or detachable dilator 50) includes what is herein referred to as a key/lock combination. In the present depiction, the key 51-k comprises a "T" shaped member for inserting into a similarly shaped lock 10a-l provided by instrument base 10a. Once the key 51-k is inserted into lock 10a-l, the exemplary sizer-dilator 51 is then rotated or twisted orthogonally with respect to the longitudinal axis of instrument 10 such that the "T" shaped member is then substantially rotated by 90 degrees from its original insertion orientation.

Still referring to FIG. 4A, as will be clear to those familiar with the lacrimal occlusion process, a sizer is necessarily similar in diameter to a dilator, as both must essentially fit into the patient's punctum. A traditional punctal sizer is a cylindrical shape that is not increasing in diameter starting at the distal end. Therefore, a traditional single punctal sizer instrument typically includes two opposing ends, where the first end includes a cylinder shape of a first diameter and the second end includes a cylinder shape of a second diameter. Given that the punctum sizes of typical patients range between at least four different orifice diameters, such as 0.2 mm, 0.4 mm, 0.6 mm and 0.8 mm, it is typically necessary for the practitioner to have at least two and often three separate punctal sizer tools for use when determining the size of the patient's punctum (see step 101 in FIG. 2 and FIG. 3). As will be clear to those familiar with the lacrimal occlusion process, having a single sizer tool, or a removable sizer-dilator such as 51 comprising a sizer profile 51-p1 sufficient for distinguishing between two or more distinct sizes offers significant advantage to be discussed further with respect to upcoming FIG. 5. The depicted sizer profile 51-p1 of the present figure with an elongated conical shape is more convenient and efficient than working with multiple tools.

The preferable sizer, such as sizer-dilator 51, further includes multiple size markings such as size 1 marking 51-m1, size 2 marking 51-m2, size 3 marking 51-m3 and size 4 marking 51-m4, where for example the segment of the elongated conical shape marked as 51-m1 has a maximum diameter of 0.2 mm, while the segment of the elongated conical shape marked as 51-m2 has a maximum diameter of 0.4 mm, the segment of elongated conical shape marked as 51-m3 has a maximum diameter of 0.6 mm, and the segment of elongated conical shape marked as 51-m4 has a maximum diameter of 0.8 mm.

Still referring to FIG. 4A, in the anticipated use of sizer-dilator 51 attached to instrument 10 base 10a, the practitioner first inserts the sizer-dilator 51 (in step 301-303, FIG. 5) into the patient's punctum, continuing to insert sizer-dilator 51 up and until it is recognized that the sizer-dilator 51 has substantially filled the orifice of the punctum. Once reaching this substantially filled depth, the practitioner determines preferably a color of the marked segment such as 51-m1, 51-m2, 51-m3 or 51-m4 that is best representative of the size of the punctum's orifice, where after the practitioner is then able to select an appropriately sized plug such as 60-1, 60-2, 60-3 or 60-4, respectively. It is further anticipated that at least some portion of the plugs such as 60-1, 60-2, 60-3 or 60-4 are also color coded or marked in a matching scheme with the markings 51-m of sizer-dilator 51.

Referring next to FIG. 4B, there is shown on the left a reference art drawing for the traditional substantially cylindrical, single size punctal-sizer instrument, where the instrument is inserted into the patient's punctum to test the "resistance" provided by the punctum to the substantially cylindrical shape, where each shape is a different "gauge size". The correct gauge size gives the correct resistance upon both entering and exiting the punctum, where the resistance is fundamentally a judgment made by the practitioner. As will be clear to the careful observer, the combination of for example a small, medium and large gauge size tools is a discontinuous measurement system, whereas the profile 51-p1 described in FIG. 4A is a continuous profile capable of determining sizes without resorting to increments such as small, medium and large, and therefore accommodates punctum sizes that are essentially in between for example small and medium, or medium and large.

Still referring to FIG. 4B, to the right of the reference art drawing there is shown an alternative sizer-profile 51-p2 for use with the sizer-dilator 51 (or even a non-detachable version of sizer-dilator 51). Rather than providing an elongated conical shape continuously and smoothing increasing in diameter starting at the distal tip proceeding at least part way towards the base of sizer-dilator 51 as depicted in FIG. 4A, the sizer-profile 51-m2 commences on the far distal end with an optional dilator tip 51-t, followed by at least one and preferably at least two distinct substantially cylindrical shaped profiles, for example substantially similar to the profiles shown in the reference art drawing of the present figure such as small, medium and large. The present invention further anticipates providing for a traditional separate sizer tool that includes two or more different gauge sizes on a single end of the tool. Those familiar with the lacrimal occlusion process will recognize the benefit of using a traditional separate sizer instrument that has been so adapted to have a profile including at least two gauge sizes (such as presently depicted as profile 51-p2) as this increases the efficiency of the practitioner whereby choosing for example a further adapted separate traditional sizer tool that includes the sizes small and medium on one end of the instrument and medium and large on the other end at least reduces the number of separate sizer tools thus making the overall procedure more efficient.

Based upon a careful consideration of the teachings presented herein, especially those familiar with the lacrimal occlusion procedure and furthermore with traditional sizer instruments for use in determining the size of the patient's punctum will recognize that multiple various profiles such as 51-p1 or 51-p2 are possible without departing from the spirit of the invention, and as such the present depictions of sizer profiles 51-p1 and 51-p2 should be considered as exemplary, rather than as limitations of the present invention.

Figure 5:
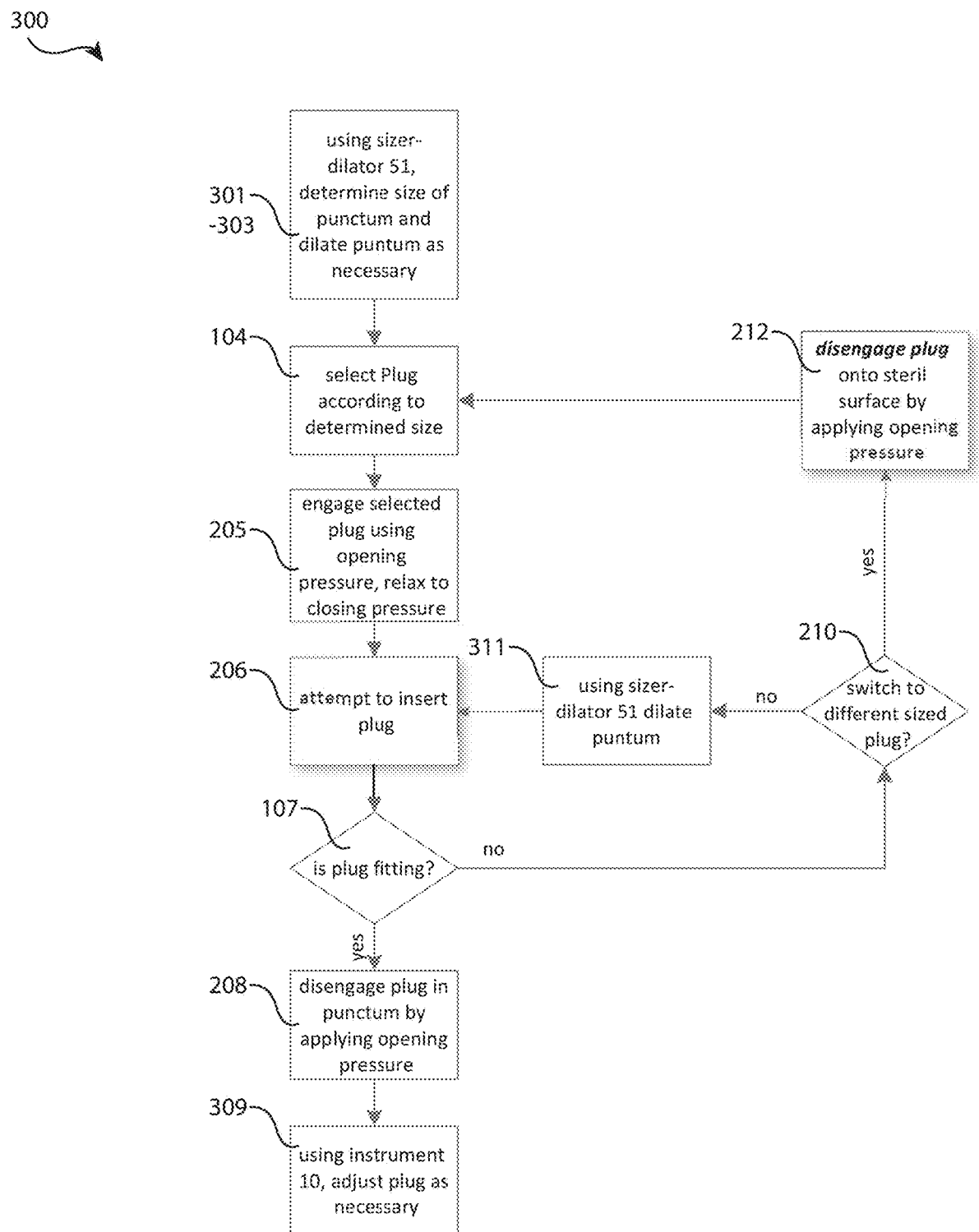
FIG. 5 is a flow chart describing the steps involved with the lacrimal occlusion process 300 according to the present invention, where process 300 relies upon the use of only one distinct tool that is the present medical instrument 10 such as depicted in FIG. 4 including sizer-dilator 51 as opposed to the dilator 50 shown in FIG. 1. Instrument 10 that has been further adapted to include sizer-dilator 51 provides for all of the functions of process 300 including punctal sizing, punctum dilation and plug engagement, insertion and disengagement.

Referring next to FIG. 5, there is shown a flow diagram describing the basic steps for performing the lacrimal occlusion process 300 using the preferred and herein taught medical instrument 10 that has been further adapted to use a sizer-dilator 51 (depicted in FIGS. 4A and 4B) as opposed to dilator 50 (depicted in FIG. 1). A careful comparison with process 200 depicted in FIG. 3 will show the following differences between process 300 and process 200. The major difference is that steps 101 (using sizer instrument, determine size of punctum), 102 (should punctum be dilated) and 103 (using dilator 50 on instrument 10, dilate punctum) have been replaced by a single step 301-303.

This is referred to as a single step (301-303) because it is accomplished using a single further adapted instrument 10, rather than a separate traditional punctal sizer and an instrument 10 as described for use in process 200. To further highlight the benefit of providing a single instrument 10 capable of providing both the punctal sizing and punctal dilation functions, it should be understood that in traditional practice there is not one punctal sizer tool but often at least a set of three separate punctal sizers, where each punctal sizer in the set accommodates two distinct sizes, one size on each of the instrument's end points. By providing a single sizer-dilator 51 on instrument 10 with a continuous profile such as 51-*p*1 it is now possible to cover at least two or more punctal sizes with a single detachable sizer-dilator 51. In an ideal situation the continuous profile 51-*p*1 is usable to determine the entire range of punctal sizes (e.g. 0.2 mm through 0.8 mm) and as such a single instrument 10 is further adapted to include such an ideal profile sizer-dilator 51 as either a detachable sizer-dilator 51 using a key-and-lock (as depicted in FIG. 4A) or alternative detachable mechanism or a permanently affixed sizer-dilator 51 (similar to dilator 50 as depicted in FIG. 1.)

Still referring to FIG. 5, if an ideal sizer-dilator 51 profile is used, then step 301-303 is accomplished with a single tool 10 as taught herein, where the practitioner commences the process 300 in step 301-303 by solely using the further adapted instrument 10 including a sizer-dilator such as 51 with a single ideal profile. In a variation of process 300, it is also possible that the entire range of possible punctum sizes is divided into N ranges, where a range N includes at least 2 of the traditional sizes, such as small and medium, or 0.4 mm and 0.6 mm. Each of the N ranges therefore preferably includes a unique sizer-dilator 51 with a profile such as 51-*p*1 or 51-*p*2 covering the traditional sizes of that range. Each of these unique sizer-dilators 51 is then preferably in a detachable form (such as the key-lock form depicted in FIG. 4A) such that in a first step 301 (i.e. rather than a combined step 301-303) the practitioner makes a visual judgment and selects the anticipated best detachable sizer-dilator 51 for attaching to instrument 10 as a part of performing a separate step 301. If the visual judgment selection is correct, then the practitioner is able to both determine the punctal size and dilate the punctum using the selected sizer-dilator 51 that has been attached to instrument 10. If the visual judgement selection is incorrect, then the practitioner disengages the first selected sizer-dilator 51 in favor of a second selected sizer-dilator 51 accommodating different traditional sizes. As a careful consideration will show, as the total number of ranges N decreases, meaning that each range includes more possible punctal sizes, the number of possible separate sizer-dilator 51 choices decreases, where again, the ideal is a single range such that N=1 and covers all sizes.

Referring still to FIG. 5, a careful consideration will show that it is also possible that the N ranges are overlapping in size, for example a first range covers sizes 0.2 mm-0.5 mm, a second range covers sizes 0.4 mm-0.7 mm and a third range covers sizes 0.6 mm-0.9 mm. In such an arrangement, the practitioner's judgment call is made simpler since for example the practitioner could consider the first range to be "small", the second range to be "medium" and the third range to be "large", where the presumption is that the majority of the time the practitioner is then able to make a visual examination of the patient's punctum and then properly select the correct small, medium or large punctal sizer-dilator 51 thus accomplishing step 301-303 using a single instrument 10. It should also be noted that it is possible that the practitioner has in this example 3 distinct instruments 10, each distinct instrument 10 with a different small, medium or larger sizer-dilator 51 that is permanently attached. Using three instruments then avoids the requirement of selecting a detachable sizer-dilator and then attaching the sizer-dilator 51 to the instrument 10 prior to use. As will be understood by those familiar with the lacrimal occlusion process, creating a combined instrument 10 that preforms all of the sizer, dilator and plug insertion functions has significant advantages and that of the many variations discussed herein, there are different benefits to each variation. As will also be clear, other variations are possible while still staying within the spirit of a 3-in-1 lacrimal plug inserter.

And finally, still referring to FIG. 5, process 300 after step 301-303 is substantially identical to process 200 with only the small exception that process 200 step 211 (using dilator 50 on instrument 10, dilate punctum) is replaced with process 300 step 311 (using sizer-dilator 51 on instrument 10, dilate punctum).

Figure 6A:
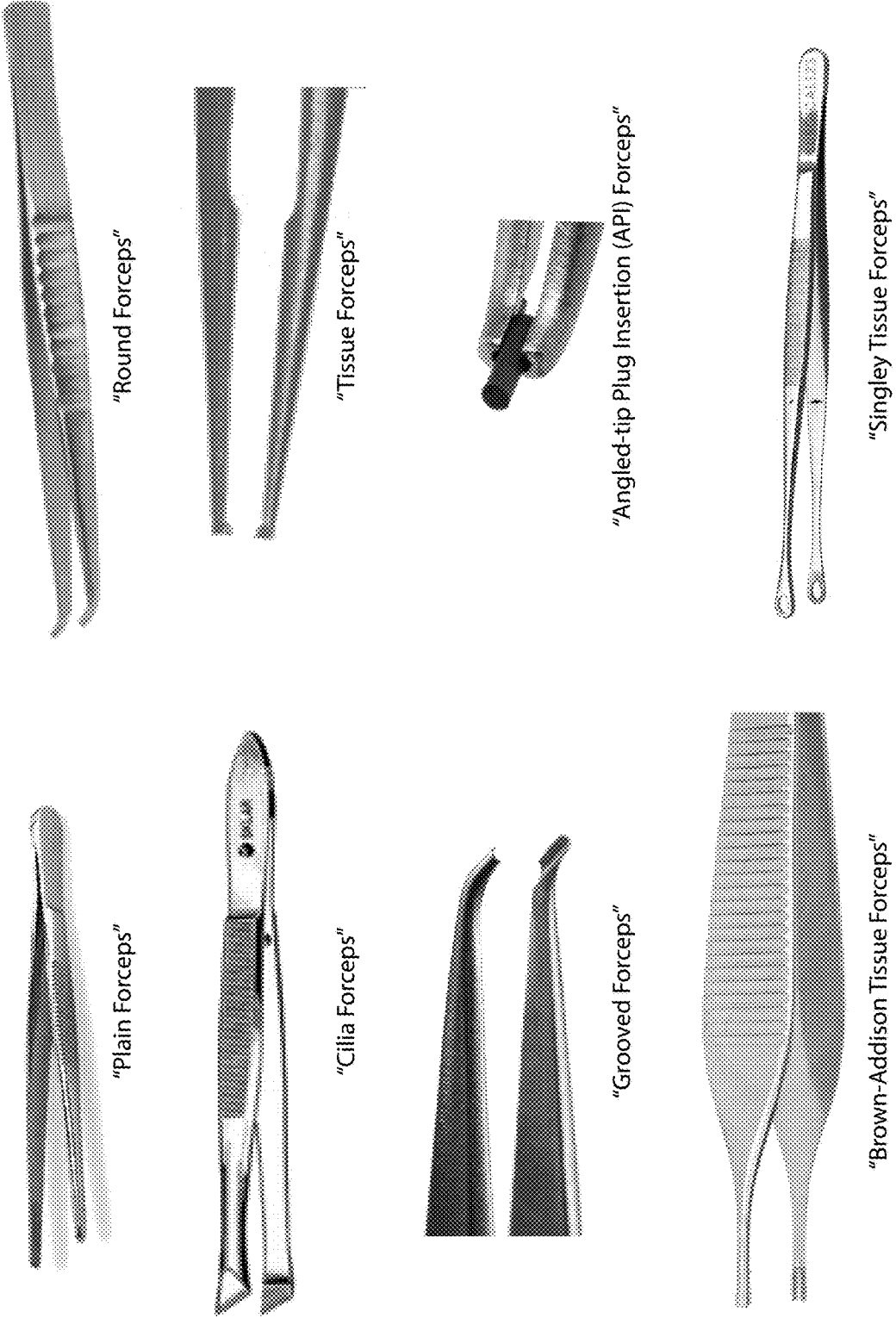
FIG. 6A depicts eight various types of thumb forceps known in the art, and more specifically depicts different forms of distal ends (herein also called tips) found to be useful for either the lacrimal occlusion procedure, such as the "angled-tip plug insertion (API)" tip, or other various medical procedures such as "cilia" tip for performing trichiasis, where any of these same or similar tips, or indeed any of the many distal ends known in the art, may be incorporated with the present invention.

FIG. 6A depicts eight various types of thumb forceps known in the art, and more specifically depicts different forms of distal ends (herein also referred to as "tips") found to be useful for either the lacrimal occlusion procedure or other various medical procedures, where any of these same ends may be incorporated with the present invention. Thus, as will be clear to those skilled in the art, the present invention may be further adapted to include other types of distal ends for example as found on traditional thumb forceps whereby the other advantages of the present instrument 10 are then combined with the advantages of the existing art instrument distal ends. For example, the distal ends 28 and 48 of the present invention 10 as depicted and described in relation to FIGS. 1 and 113 can alternately be implemented to look and function substantially like what is referred to in the art as an "angled-tip plug Insertion (API)" tip, whereby instrument 10 is still intended for use in the lacrimal occlusion medical procedure. Alternatively, the prior described distal ends 28 and 48 could be implemented to look and function substantially like what is referred to in the art as a "cilia" tip, whereby instrument 10 has therein been further adapted for use in the medial procedure referred to as trichiasis.

What is important to see is that there are many benefits herein taught with respect to instrument 10, wherein these benefits are not strictly relegated to the form of distal ends 28 and 48, as many forms are possible and will be apparent to those skilled in the art, especially with respect to the lacrimal occlusion procedure, but also with respect to other medical procedures, and even to non-medical procedures. Thus, in keeping with the spirit of the invention, the various instrument 10 parts depicted herein such as distal ends 28 and 48, proximal end dilator 50 or sizer-dilator 51, or even arms 2 and 4 should be considered as exemplary rather than as limitations of the present invention. Those skilled in the art of medical instruments will realize that each of the various parts of instrument 10 described herein may be altered with respect to form or material construction without departing from the intentions and purposes of the respective parts, and therefore many variations are anticipated.

Referring next to FIG. 6B, there is shown a perspective drawing of medical instrument 10 that has been further adapted to allow instrument 10 to function with an interchangeable range of possible distal end tips, such as those depicted in FIG. 6A. In reference to prior FIG. 1, holding surface 10d was taught to be formed by the distal ends 28 and 48 of arms 2 and 4, respectively, where in FIG. 1 distal ends 28 and 48 where non-detachable (i.e. permanent). In the present FIG. 6B, distal end 28 of arm 2 has been further adapted to include permanent base 28-base for receiving any of detachable tips such as "cilia" style tip 28-tip1. Likewise, distal end 48 of arm 4 has been further adapted to include permanent base 48-base for receiving any of detachable tips such as "cilia" style tip 48-tip1. As will be clear from a careful consideration of the present figure and the teaching provided herein, instrument 10 may be implemented with any combination of: 1) a permanent proximal end such as dilator 50 depicted in FIG. 1 or an interchangeable proximal end for receiving for example detachable sizer-dilator 51 including any number of profiles such as 51-p1 or 51-p2, and 2) a permanent distal end such as distal ends 28 and 48 depicted in FIG. 1 or an interchangeable distal end including bases 28-base and 48-base, respectively, for receiving for example detachable cilia style tips 28-tip1 and 48-tip1, respectively, or an adaptable distal end including latches for receiving tip sleeves (see upcoming FIGS. 6D, 6E, 6F, 6G and 6H).

Referring next to FIG. 6C detachable distal tip 48-tip1 is show as detached from distal base 48-base and furthermore rotated orthongally with respect to the final attached position depicted in FIG. 6B. Distal tip 48-tip1 is depicted as including an attaching member such as key 48-tip1-k while distal base 48-base is depicted as including a receiving member such as lock 48-base-l. This "key-and-lock" system is preferably the same as prior described in FIG. 4A in relation to detachable sizer-dilator 51 including key 51-k and instrument base 10a including lock 10a-l. As also prior mentioned in relation to FIG. 4A, those familiar with mechanical systems will recognize that there are many possible mechanisms for attaching a detachable distal end tip such as 28-tip1 or 48-tip1 to a base such as 28-base or 48-base, respectively, and as such the present depiction should be considered as exemplary rather than as a limitation of the present invention. It is even possible that the key-lock mechanical systems depicted in both FIG. 4A and the present FIG. 6C can be modified while still staying with the spirit of a key and lock, where for example the shapes of the key such as 48-tip1-k and lock such as 48-base-l are modified in such a way that the detachable tip such as 48-tip1 is limited to being inserted into lock 48-base-l from only one of the two possible (preferably, but not necessarily) orthogonal rotations. Furthermore, the interior (not depicted) of a lock such as 48-base-l may be shaped in such a way that after insertion of a key such as 48-tip1-k into lock 48-base-l, tip 48-tip1 may only be rotated in a single direction, for example clockwise when viewed from the distal end of instrument 10 looking towards the proximal end of instrument 10, as presently depicted.

Referring next collectively to FIGS. 6D, 6E, 6F, 6G and 6H, there is depicted a further adaptation to instrument 10 for attaching and detaching tip sleeves that substantially slide over and cover each or either of distal ends 48 and 28 in order to provide the practitioner with different optional distal end tips such as those depicted in FIG. 6A or otherwise well-known in the reference art. The figures collectively teach the adaptations to instrument 10 and introduce new tip sleeves, trays for holding tip sleeves, boxes for holding trays and racks for holding boxes.

Referring next exclusively to FIG. 6D there is shown a perspective drawing of the distal end of instrument 10, where distal end 48a and 28a have been further adapted to include latches 48a-l and 28a-l, respectively, for securing tip sleeves 49a and 29a, respectively, and where sleeves 49a and 29a further include interior companion latches (not depicted) for engaging latches 48a-l and 28a-l and exterior companion latches 49a-l and 29a-l for engaging a tray (see FIG. 6E). As will be well understood by those familiar with mechanical systems, there are many types of latches, especially those including spring action, the many of which are sufficient for the present purposes. In one embodiment as herein depicted, the distal end latch such as 48a-l comprises an indentation of some shape into which the interior companion latch (not depicted) within tip sleeve such as 49a at least partially engages, or enters, as the tip sleeve 49a is slide onto and over the distal end such as 48a. For example, the interior companion latch of sleeve 49a could be a ball mounted with an opposing spring essentially pushing the ball in the direction of the surface of distal end 48a comprising latch 48a-l. In this regard, the exact shape of distal end 48a, as well as the location on the surface of 48a, wherein a securing latch such as 48a-l (and therefore also its companion latch within sleeve 49a) is located is not restricted, as many options are available and possible. Furthermore, the number of latches 48a-l (where two are depicted although only one is labeled) and companion latches within sleeve 49a is also optional. What is most important to see is that: 1) the latch such as 48a-l operates automatically to engage the companion latch comprised within the respective tip sleeve such as 49a, for example in response to the sliding on and over of a tip sleeve such as 49a, and 2) the latch or latches such as 48a-l as well as the companion latches within sleeve 49a, in any form, number or combination, causes what is herein referred to as a sleeve holding pressure, and that collectively the latches operate together as a securing means for a replace tip such as 49a.

As a careful consideration of the teachings herein provided will see, in the normal uses anticipated for instrument 10, there is anticipated to be minimal forces opposing this sleeve holding pressure, but in any case the types, forms, locations, or number of implemented securing latches may be designed and implemented accordingly such that the combined sleeve holding pressure is sufficient to ensure that a tip sleeve such as 49a remains securely attached to its companion distal end such as 48a after engagement and during normal operation of the present instrument 10.

Still referring to FIG. 6D, it is possible that a given latch operates at least in part using a magnet either or both located or secured within the distal end such as 48a or the tip sleeve such as 49a. Still other considerations will show that the tip sleeve such as 49a may have alternate designs where the sleeve includes interior posts substantially oriented in the direction of engagement, and that these interior posts slid into interior post holes co-located within the distal end such as 48a. Conversely, the posts could be included on the distal end such as 48a, whereas the post holes could be co-located within the sleeve such as 49a. One advantage of the present depiction of latches such as 48a-l (of some type and in some form, location and number) as opposed to the co-location of one or more posts and post holes is that using this latch type design the existing distal end 48a may include a usable tip-type of its own, such as the pointed tips as shown (see also FIG. 1), as long as this usable tip is able to slide within a given tip sleeve such as 49a. Given the considerations and teachings of FIG. 6D, it should therefore be understood that the present depictions and descriptions are exemplary and should not be considered as limitations of the present invention as many variations are possible and anticipated as within the scope of the present invention.

Referring next to FIG. 6E, there is shown a perspective drawing of sleeve box 70, comprising sleeve trays 49a-t and 29a-t for receiving, holding and discharging any of sleeves 49a and 29a, respectively. Each tray 49a-t and 29a-t such as 49a-t preferably further comprises a first tray cavity 49a-tc1 for holding the non-tip portion of a sleeve such as 49a, a second tray cavity 49a-tc2 for holding the tip portion of a sleeve such as 49a, an interior latch 49a-tl for impeding the lateral exit motion of a sleeve such as 49a and a lateral tray entrance 49a-te for receiving and discharging the distal end of instrument 10 such as 48a being either inserted into or removed from a sleeve such as 49a held within tray 29a-t, all of which is further best understood in light of upcoming FIGS. 6F and 6G. Similar to the discussions respective of distal end latches such as 48a-l and 28a-l and corresponding interior companion latches (not depicted) located within tip sleeves 49a and 29a, it is possible that for example tip sleeve 49a exterior companion latch 49a-l (see FIG. 6D) and corresponding interior latch 49a-tl of tray 49a-t be of many various types, forms, locations and multiplicities.

As a careful consideration will show, the presently depicted tray interior latch 49a-tl forms a lip segregating the portion of tray 49a-t serving as the tray entrance 49a-te (that is therefore narrower in dimension) from the portion of the tray 49a-t serving as the first cavity 49a-tc1 (that is therefore wider in dimension), all as depicted. Given such an arrangement as depicted, and as further shown with respect to upcoming FIGS. 6F and 6G, the use of the present lip 49a-tl restricts the movement of any tip sleeve such as 49a resting within tray cavities 49a-tc1 and 49a-tc2 from being extracted from the tray in a lateral motion with respect to the tray's longitudinal axis, where this extraction is essentially impeded by the narrowed portion of tray entrance 49a-te with respect to the wider portion of tray cavity 49a-tc1.

Still referring to FIG. 6E, those familiar with latches specifically and mechanical systems in general will understand that many variations are possible while staying within the spirit of the present invention. What is important to see is that any tip sleeve such as 49a has an entrance/exit path into the corresponding cavities 49a-tc1 and 49a-tc2 of tray such as 49a-t of box 70 that is limited to a specific and substantially unimpeded direction, in this case perpendicular to the longitudinal axis of tray 49a-t of box 70 (see especially upcoming FIG. 6G for further discussion). As a careful consideration will show, the present and preferred design provides first and second cavities 49a-tc1 and 49a-tc2 sufficient for receiving the entirety of a tip sleeve such as 49a being lowered into (or raised from) tray 49a-t substantially unimpeded in the perpendicular direction with respect to the longitudinal axis of tray 49a-t. What is also important to see is that while resting within tray 49a-t, tip sleeve 49a can be either engaged or disengaged by a distal end of instrument 10, such as distal end 48, where this direction of engagement/disengagement is substantially different from the direction of removal/replacement (see FIG. 6G), for example being an lateral direction with respect to the longitudinal axis of tray 49a-t, where as depicted the lateral direction is substantially parallel to the longitudinal axis of tray 49a-t and therefore also substantially orthogonal to the perpendicular path of removal/replacement.

As will be clear from a careful consideration of the present FIG. 6E and related FIGS. 6D, 6F and 6G, tray latch 49a-tl effectively provides a resistive impedance for overcoming the combined sleeve holding pressure as prior described in relation to FIG. 6D, such that when the distal end such as 48a is being extracted from a corresponding and currently engaged sleeve 49a, where the sleeve 49a is already resting within tray 49a-t, the tip sleeve 49a is thereby caused by the resistive impedance of tray latch 49a-tl to disengage from the distal end 48a such that the distal end 48a is extracted from within the sleeve 49a, within the tray 49a-t, exiting through tray entrance 49a-te, whereas the tip sleeve 49a remains situated within the tray 49a-t. It should be noted that the resistive force available from tray latch 49a-tl is dependent upon the forces that secure box 70 to a surface upon which box 70 is resting during the normal use of the proposed box 70. For example, box 70 may be resting upon a rubberized mat on a table where the rubberized mat provides a frictional force that sufficiently exceeds the combined sleeve holding pressure (force) such that the box 70 does not slip or slid across the resting surface during the extraction of a distal end such as 48a from a sleeve such as 49a. Alternatively, the box 70 could be attached or mounted to the resting surface below the box, or even heavily weighted, where many variations are possible as will be well understood by those familiar with mechanical systems, all of which are considered within the scope and spirit of the present invention.

Still referring to FIG. 6E, it is preferable but not mandatory that the end of box 70 comprising entrances such as 49a-te be of a greater first height 70-h1 respective to a lesser second height of 70-h2 corresponding to the opposite end of box 70 comprising second cavities such as 49a-tc2. As a careful consideration of the present teachings will make clear, given this disparity between heights 70-h1 and 70-h2, box 70 will essentially appear to a practitioner situated on the entrance side (comprising 49a-te) of box 70 to lean down and away. As will also be clear based upon a mental visualization of the hand motions required of the practitioner with respect to the use of instrument 10 with respect to tray 70, the practitioner must rotate the instrument 10 such that the distal ends 48a and 28a are aligned side-by-side with respect to the surface upon which box 70 resides, where in this alignment it is preferred that the practitioner's hand is facing palm-up verses palm-down.

In such a palm-up orientation, the fingers and knuckles of the practitioner's hand that is holding instrument 10 are facing substantially downward and therefore not obscuring the view of the practitioner with respect to the box 70 and sleeves such as 49a and 29a resting within the box 70. Furthermore, a careful consideration will also show that by leaning the trays such as 49a-tc1 downward and away from the practitioner and the entrance such as 49a-te of box 70 (corresponding to height 70-h1 being greater than 70-h2), additional clearance space is provided for the downward facing fingers and knuckles of the practitioner's hand that is holding instrument 10. Other alternative box 70 constructions are possible without departing from the spirit of the present invention and the core teachings provided herein. For example, the heights 70-h1 and 70-h2 could be substantially similar (or even reversed where height 70-h2 exceeds height 70-h1) and the box 70 could be adapted to situated at the edge of a mounting surface (such that the practitioner's fingers do not encounter the surface as the practitioner's hand moves the distal ends 48a and 28a of instrument 10 into their respective tray entrances such as 49a-te (and a similar 29a-te not depicted). Alternatively, the box 70 could have downward facing mounting posts or be enlarged to increase the effective distance between the bottommost interior height of a tray such as 49a-t and the surface upon which the box 70 is situated, thereby also or additionally creating further clearance for the practitioner's downward facing fingers. And finally, its is possible that box 70 comprise a single tray such as 49a-t and therefore comprises no second tray such as 29a-t, wherein for example instrument 10 has only a single replaceable distal end such as 48a (and therefor 28a is obviated in favor of distal end 28 without securing means) or both distal ends 48a and 28a are included in instrument 10 where the practitioner chooses to fasten a single tip sleeve such as 49a at a time, where it should then be seen by a careful consideration that a single tray such as 49a-t holding a single sleeve such as 49a could service either distal end such as 48a or 28a. Thus, the presently depicted box 70 (and upcoming rack of boxes 72 shown in FIG. 6H) should be considered as exemplary, rather than as a limitation of the present invention as many variations are possible and anticipated without departing from the spirit of the invention.

Referring next to FIG. 6F, there is shown a perspective view of instrument 10 further adapted as described in FIG. 6D to comprise distal ends 48a and 28a partially inserted into sleeves 49a and 29a, respectively, where sleeves 49a and 29a are being held within trays 49a-t and 29a-t, respectively, comprising sleeve box 70 as described in FIG. 6E. The purpose of FIG. 6F is to provide an additionally clarifying perspective view of tray 70 as described in FIG. 6E holding tip sleeves 49a and 29a as described along with partially inserted instrument 10 distal ends 48a and 28a all as described in FIG. 6D.

Referring next to FIG. 6G, there is shown a side view diagram depicting three steps 1, 2 and 3 for first inserting (steps 1 and 2) via substantially a lateral motion distal ends such as 48a comprising latch 48a-l into sleeves such as 49a held within sleeve box 70, and second removing (step 3) via substantially a perpendicular motion sleeves such as 49a now secured via an interior latch (not depicted) to a distal end latch such as 48a-l, where in the perpendicular motion exterior latch 49a-l of sleeve 49a is substantially unimpeded by tray box 70, and where the combination of steps 1, 2 and 3 is pictorially shown as "engage" and "remove". Whereas steps 1, 2 and 3 allow for the engagement and removal of sleeves such as 49a from the tray box 70 by instrument 10, a reversal of steps 1, 2 and 3 further allow for the "replacement" and "disengagement" of sleeves such as 49a from tray box 70 by instrument 10, wherein during the reversal of step 3 tray box 70 substantially impedes the removal of a sleeve such as 49a by catching exterior companion latch 49a-l during the extracting lateral motion, thereby disengaging a sleeve such as 49a from a distal end such as 48a.

Figure 6H:
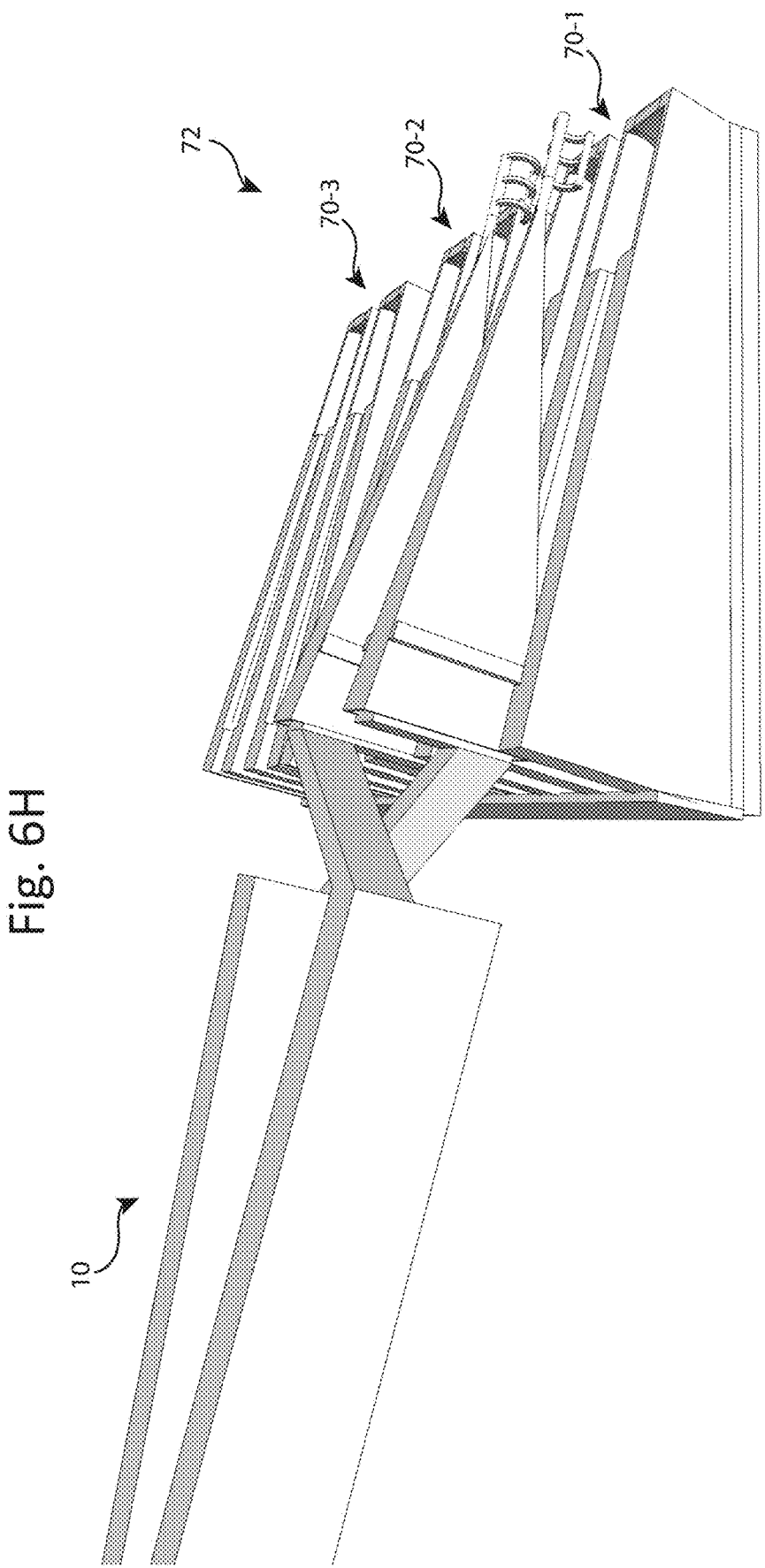
FIG. 6H is a side-perspective view of a tray rack 72 for example comprising three tray boxes 70-1, 70-2 and 70-3, where instrument 10 is depicted as removing (or replacing) sleeves from tray box 70-1 in accordance with the steps 1, 2 and 3 described FIG. 6G.

Referring next to FIG. 6H, there is shown a side-perspective view of a tray rack 72 for example comprising three tray boxes 70-1, 70-2 and 70-3, where instrument 10 is depicted as removing (or replacing) sleeves from tray box 70-1 in accordance with the steps 1, 2 and 3 described FIG. 6G. As will be obvious to those skilled in the arts for which the instrument and tip sleeves are intended, such as but not limited to one or more medical or non-medical applications including the lacrimal occlusion procedure, the number of trays such as 70-1, 70-2 and 70-3 in a given rack such as 72 may be varied as desirable without departing from the scope and spirit of the present invention. Many other rack 72 designs are possible, where the number and size of trays such as 70-1 are varied, as well as their relative arrangements. It is not mandatory that the racks such as 70-1, 70-2 and 70-3 are in a horizontal arrangement and can alternately or additionally be provided in a vertical arrangement, although such an arrangement must necessarily leave sufficient space over each tray for ease of tip sleeve replacement and removal. Therefore, the presently depicted rack 70 should be considered as exemplary, rather than as a limitation of the present invention, as many other configurations of trays are possible and anticipated.

Referring next collectively to FIGS. 7A, 7B, 8A, 8B, 9A, 9B, 10A and 10B, there are depicted four different mechanisms for providing the function of clamp-limiting, where the holding surface 10d is mechanically blocked from completely closing given the absence of any engaged plug such as 60 or 61. As prior discussed, unlike thumb forceps where the closing pressure is applied by the practitioner as a continuous pressure to be maintained throughout at least the plug insertion step 106 (see FIG. 2), the present instrument 10 provides inherent positive (closing) pressure between distal ends 28 and 48 such that the practitioner only maintains holding pressure to maneuver the instrument 10 during plug insertion step 206 (see FIG. 3), regardless of the form of the distal ends such as pointed, rounded, curved, or any of the various reference art shapes including those depicted in FIG. 6A, and regardless of the type of the distal ends such as permanent (FIG. 1) versus detachable (FIGS. 6B, 6C, 6D, 6F and 6G). As those familiar with plugs and the lacrimal occlusion medical procedure, as well as other medical procedures for which a clamping action is desired, the ability to limit the clamping pressure for example when engaging a larger sized plug made of a softer material has significant advantages.

Figure 7A:
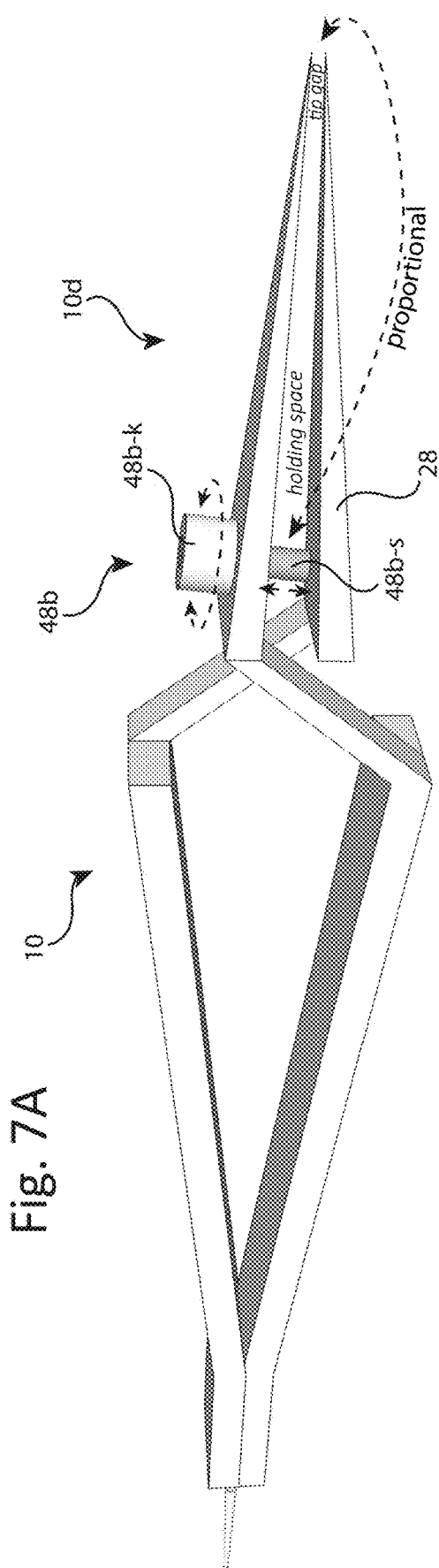
FIGS. 7A and 7B depict the distal end 48 of presently taught medical instrument 10 that has been further adapted as distal end 48b comprising a screw type clamp-limiting means including knob 48b-*k* for turning by the practitioner, where turning the knob 48b-*k* causes screw 48b-*s* to raise or lower commensurately into the holding space between distal ends 48b and 28, thereby proportionately effecting the tip gap and associated closing (positive) pressure of instrument 10. Also depicted are markings 48b-*m* for indicating the direction and amount of turning of knob 48b-*k* that corresponds to desired plug sizes as prior determined using a sizer-dilator with associated markings on profile 51-*p*1 (see FIG. 4A).

Referring next exclusively to FIG. 7A, there is shown distal end 48b that has been further adapted to include a first clamp-limiting screw type mechanism that includes a knob 48b-k for turning by the practitioner. As those familiar with screw action will understand, as the practitioner turns the knob 48b-k both the knob 48b-k and screw 48b-s extending from the knob 48b-k are either lowered into the holding space between distal ends 48b and 28 or are raised out of the holding space between distal ends 48b and 28. As will be clear from a careful consideration of the present figure, the length of the screw 48b-s present in the holding space has a proportional effect on the tip gap between the distal ends, such that by limiting the tip gap to some non-zero amount, where with a zero amount gap distal end 48b comes into contact with distal end 28, it is possible to thereby limit the clamping pressure.

Figure 7B:
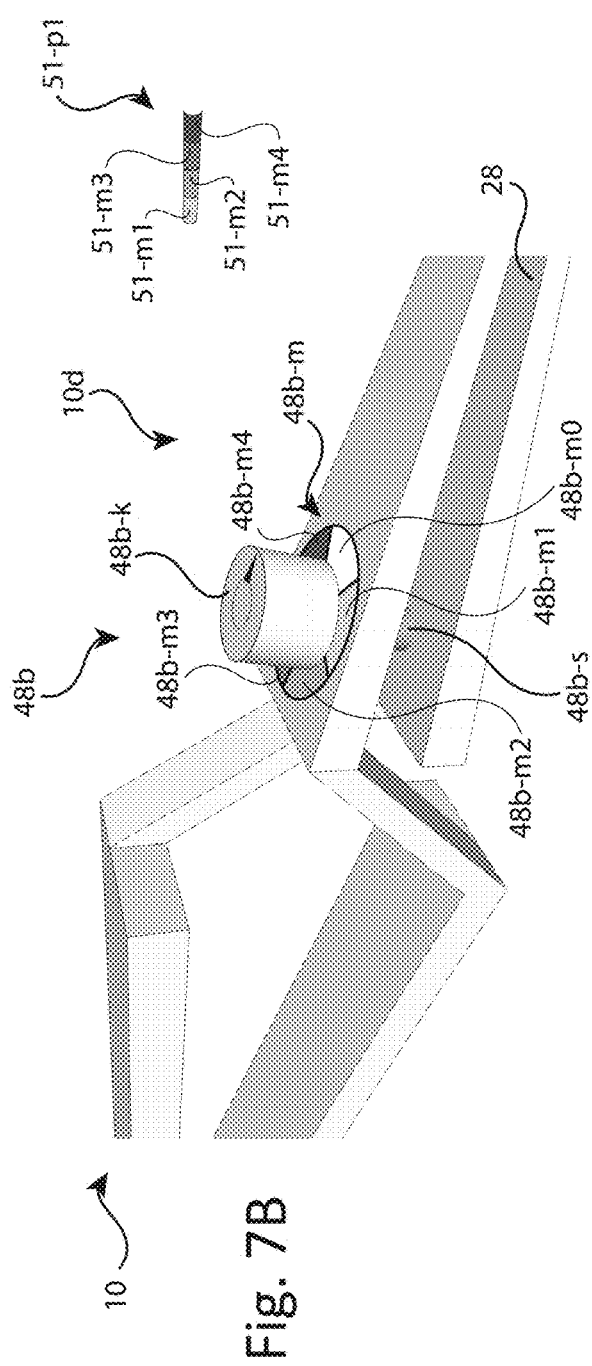

Referring next exclusively to FIG. 7B, distal end 48b has been further adapted to include markings 48b-m including 48b-m1, 48b-m2, 48b-m3 and 48b-m4 for corresponding with sizer markings such as 51-m1, 51-m2, 51-m3 and 51-m4, respectively (see also FIG. 4A). Preferably, markings 48b-m also include a marking 48b-m0 representing a zero-amount gap (that does not have a corresponding 51-m0 marker), where marking 48b-m0 represents the fully closed tip gap as opposed to markings 48b-m1, 48b-m2, 48b-m3 and 48b-m4, each corresponding to some non-fully-closed tip gap. As will be clear from a careful consideration of the present figure, by arranging the markings 48b-m around the knob 48b-k and by including a mark on the top surface of the knob for indicating the current turning position (see the dark triangle), it is possible to provide the practitioner with a visible indication as to the amount of knob turning necessary to reach a desired tip gap based upon for example the size of the punctum as determined using a sizer-dilator 51 with markings 51-m1, 51-m2, 51-m3 and 51-m4. As will be clear to those familiar with mechanical systems and medical tools, other variations of markings such as 48*b-m* are possible without departing from the spirit of the invention, and as such the present markers depicted, including the number of markings such as 48*b-m*0, 48*b-m*1, 48*b-m*2, 48*b-m*3 and 48*b-m*4, as well as at least the color, size, shape and location of the markings 48*b-m* should be considered as exemplary, rather than as a limitation of the present invention.

Referring next collectively to FIGS. 8A, 8B, 9A, 9B, 10A and 10B, it is herein noted that for the sake of clarity and focus on the depicted clamp-limiting mechanisms, no markings like 48*b-m* such as 48*b-m*0, 48*b-m*1, 48*b-m*2, 48*b-m*3 and 48*b-m*4 have been depicted in these upcoming figures. However, the present invention anticipates the use of some type of markings such as 48*b-m* depicted in FIG. 7B for each of the various clamp-limiting means herein taught with respect to FIGS. 8A, 8B, 9A, 9B, 10A and 10B, such that regardless of the type of clamp-limiting means implemented in the instrument 10, markings such as 48*b-m* are made available to assist the practitioner with setting the mechanical clamp-limiting mechanism to correspond to a determinized size of for example a punctum orifice. As will be clear upon a careful consideration of the upcoming clamp-limiting means as depicted in FIGS. 8A, 8B, 9A, 9B, 10A and 10B, many variations of markings such as 48*b-m* are possible and further anticipated within the spirit of the present teachings.

Referring next to FIGS. 8A and 8B, there is shown an alternative distal end 48*c* that has been further adapted to include mechanical means for limiting the clamping pressure of instrument 10, where the mechanical means is a sliding wedge 48*c-w* that is moved forward by the practitioner pushing the sliding wedge knob 48*c-k* towards the distal end of instrument 10 to widen the tip gap (and therefore further limit the closing pressure), and is moved backward by the practitioner pulling the sliding wedge know 48*c-k* away from the distal end of instrument 10 to narrow the tip gap (and therefore further increase the closing pressure).

Referring next to FIGS. 9A and 9B, there is shown an alternative distal end 48*d* that has been further adapted to include mechanical means for limiting the clamping pressure of instrument 10, where the mechanical means is a rotating oblong wheel 48*d-w* that is rotated for example clockwise by the practitioner likewise rotating knob 48*d-k* clockwise to widen the tip gap (and therefore further limit the closing pressure), and is rotated for example counter-clockwise by the practitioner likewise rotating knob 48*d-k* counter-clockwise to narrow the tip gap (and therefore further increase the closing pressure).

Figure 10A:
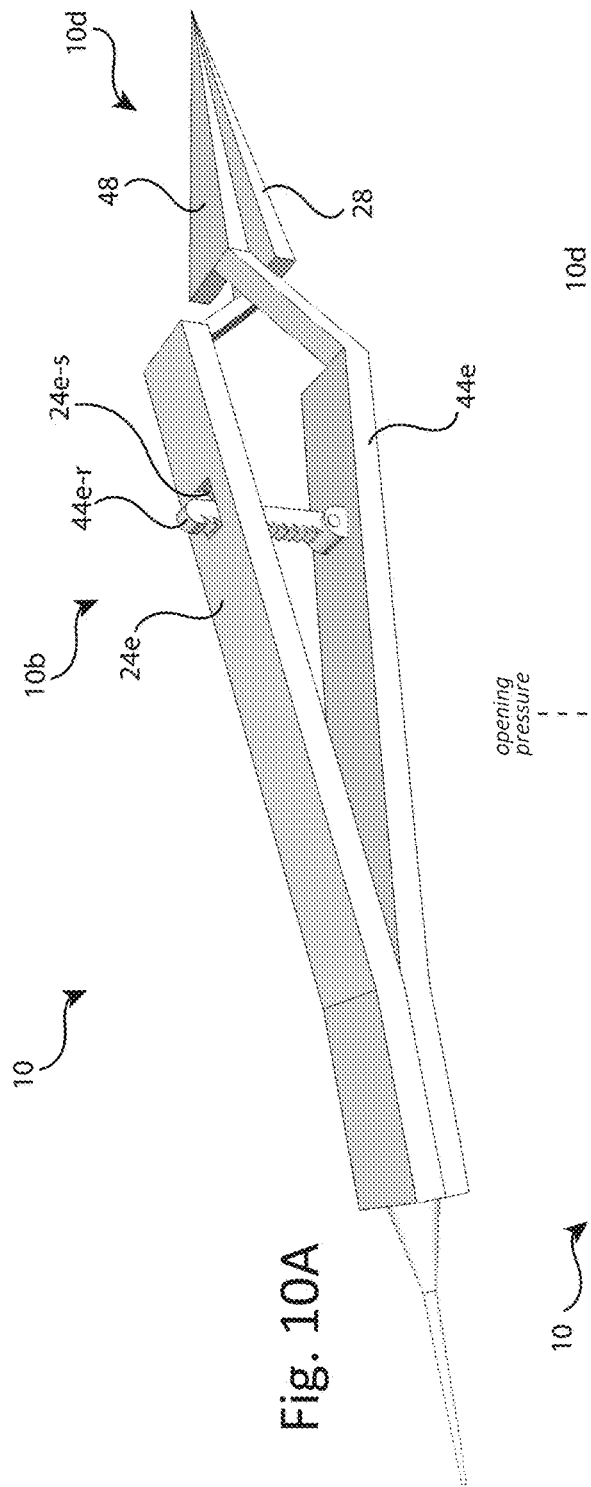
FIGS. 10A and 10B depict the wide portions 24 and 44 of presently taught medical instrument 10 that have been further adapted as wide portions 24e and 44e comprising a rachet type clamp-limiting means including pivoting rachet arm 44e-*r* in combination with return pressure spring 24e-*s*, where, as the practitioner applies normal opening pressure upon wide portions 24e and 44e rachet combination 44e-*r* and 24e-*s* causes the wide portions 24e and 44e to essentially remain fixed at the closest separation of portions 24e and 44e obtained prior to the release of the opening pressure by the practitioner, thereby inverse proportionately effecting the tip gap and associated closing (positive) pressure of instrument 10.
Figure 10B:
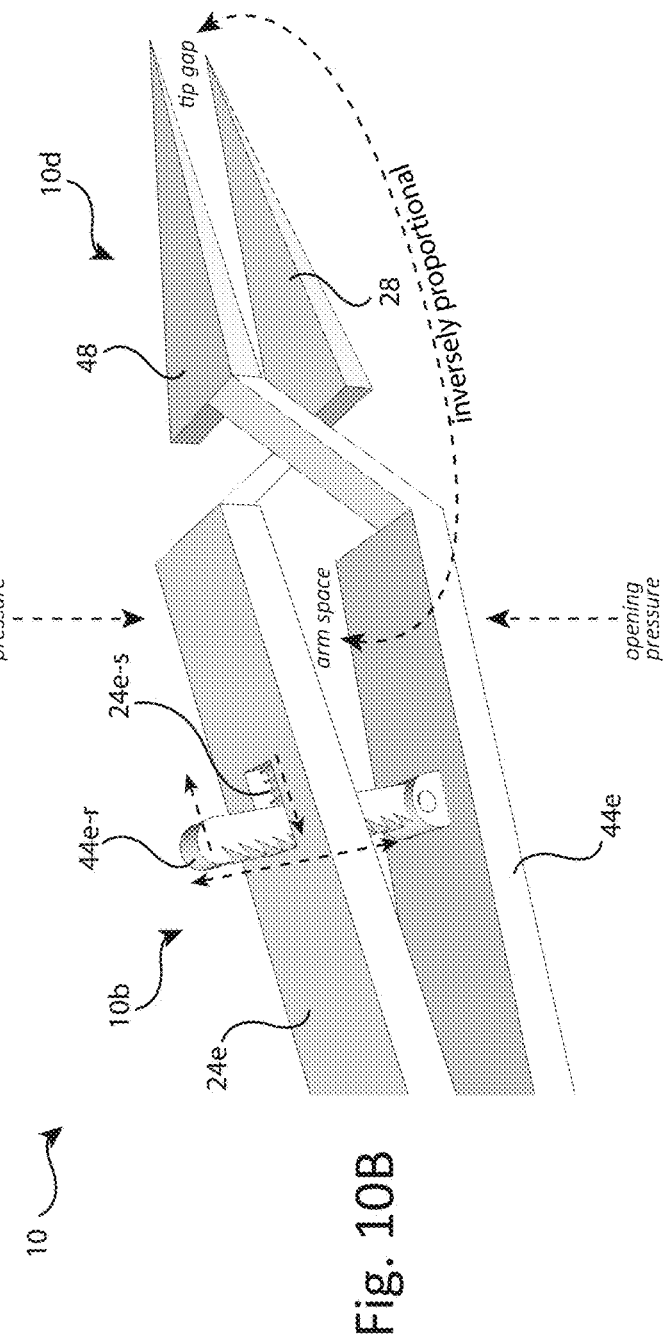

Referring next to FIGS. 10A and 10B, there is shown alternative wide portions 24*e* and 44*e* comprising grasping surface 10*b* that have been further adapted to include mechanical means for limiting the clamping pressure of instrument 10, where the mechanical means is pivoting rachet arm 44*e-r* pivotally attached to wide portion 44*e* that slides through an opening in wide portion 24*e* as the practitioner exerts an opening pressure (as prior described in relation to FIG. 1) upon wide portions 24*e* and 44*e* so as to reduce the arm space and inversely increase the tip gap, and where the mechanical means further includes a return pressure means such as spring 24*e-s* located within the opening in wide portion 24*e* that applies return pressure upon rachet arm 44*e-r* so as to cause rachet arm 44*e-r* to catch and re-catch upon wide portion 24*e*, all as will be well understood by those familiar with a rachet mechanism. The effect of the operation of rachet 44*e-r* and spring 24*e-s* is that as the practitioner releases the applied opening pressure upon wide portions 24*e* and 44*e* spring 24*e-s* causes the rachet 44*e-r* to catch up wide portion 24*e* such that the normal inherent closing (positive) pressure of the bulldog forceps is impeded, thus fixing the arm space and therefore tip gap at a distance substantially determined by the extent of the opening pressure applied by the practitioner. In order to restore the maximal closing (positive) pressure inherent within the design of instrument 10, the practitioner exerts a forward pressure upon the portion of rachet 44*e-r* protruding through the opening in wide portion 24*e* that moves the rachet 44*e-r* forwards towards the distal end of instrument 10, where this exerted forward pressure counteracts and overcomes the return pressure applied by spring 24*e-s* thus allowing wide portions 24*e* and 44*e* to fully separate increasing the arm space to a maximum while inversely decreasing the tip gap to a minimum.

Referring next to FIGS. 11A and 11B, the distal ends 28 and 48 of rachet type clamp-limiting medical instrument 10 as taught in relation to FIGS. 10A and 10B have been further adapted as distal ends 28*tip*2 and 48*tip*2 including tissue separating style tips. As those familiar with medical instruments will understand, there are multiple designs currently known and otherwise possible for facilitating the tissue separating function and therefore the present depictions should be considered as exemplary rather than as a limitation of the presentation invention. What is important to see is that the medical instrument 10 that has been further adapted with a rachet style clamp-limiting means such as taught in relation to FIGS. 10A and 10B provides a means for separating tissue substantially proportional to the amount of opening pressure applied by a practitioner to wide portions 24*e* and 44*e*, where increased opening pressure causes increased separating pressure applied on the tissue (or matter to be separated) by distal tips 28*tip*2 and 48*tip*2. Once a preferred tissue separation pressure and therefore also tissue separation distance has been achieved by the practitioner in operation of the further adapted instrument 10 as presently depicted and described especially in relation to FIGS. 10A and 10B, the included rachet mechanism serves to lock-in the substantially final separation of distal end 28*tip*2 and 48*tip*2. Also, as prior discussed, the practitioner releases this final applied separating pressure thus reducing the final achieved separating distance between distal end 28*tip*2 and 48*tip*2 by exerting a forward pressure upon the portion of rachet 44*e-r* (see the teachings in relation to FIGS. 10A and 10B), thus disengaging the rachet.

CONCLUSION AND RAMIFICATIONS

Thus, as the reader can see, the present two-in-one inventive medical instrument 10 and lacrimal occlusion process 200 includes at least the following improvements with respect to process traditional process 100: 1) increasing the continuous concentration and focus of the practitioner thus reducing the likelihood of inadvertent physical harm to the patient; 2) reducing the practitioner's physical muscle stresses and potential attendant hand shaking by eliminating the need for applying continuous closing pressure while simultaneously moving the instrument 10 for plug insertion; 3) reducing the overall mental stresses on both the patient and the practitioner; 4) reducing the likelihood of dropping plugs and therefore decreasing the average material cost to the practitioner, and 5) reducing the average process time duration and therefore also average time cost to the practitioner. Other important benefits have been detailed herein and will be obvious to those skilled in the art of lacrimal occlusion.

Furthermore, based upon the further adaptation of medical instrument 10 providing for a combined sizer-dilator 51, and thus a three-in-one tool, the reader can see that the lacrimal occlusion process 300 includes at least the following improvements with respect to process 200: 1) further increasing the continuous concentration and focus of the practitioner thus reducing the likelihood of inadvertent physical harm to the patient; 2) further reducing the overall mental stresses on both the patient and the practitioner, and 3) further reducing the average process time duration and therefore also average time cost to the practitioner.

As the reader will also see, the present instrument 10 further provides for permanent or detachable proximal or distal ends, where for example based upon the orientation of the instrument 10 the proximal ends could be a dilator 50 or a sizer-dilator 51 and the distal ends could be any of various end tips such as 48-*tip*1 or 28-*tip*1, or end tip sleeves such as 49*a* or 29*a*, where the shape and function of these various end tips and tip sleeves can at least match any of the shapes and functions currently used in the reference art for various medical procedures including lacrimal occlusion, trichiasis, and tissue separation. Those skilled in other non-medical arts will recognize that the many teachings of the present invention provide significant benefits for non-medical uses. With respect to the detachable distal end sleeves 49*a* and 29*a*, the present reader will also see that a new system has been provided for allowing the practitioner to efficiently select, replace or switch between a number of different end tip sleeves using only a single hand, thus further facilitating the optimization of at least medical procedures such as lacrimal occlusion. This new system comprises at least one box 70 comprising two trays 49*a*-*t* and 29*a*-*t*, where each tray holds a replaceable sleeve 49*a* or 29*a*, respectively, for one of the instrument's 10 distal ends such as 48*a* or 28*a*, respectively. It is further anticipated herein that this same teaching for replaceable distal end tips complete with the rack, box and tray system, is also applicable for implementation with the detachable proximal ends, hence supporting multiple dilators or sizer-dilators. This anticipated further adaptation thus additionally provides for allowing the practitioner to efficiently select, replace or switch between a number of different dilators or sizer-dilators using only a single hand. In one distinction, the proximal end tray system only requires one tray per box, as will be obvious to the careful reader.

And finally the reader will also see that the present teachings provide mechanical means for allowing the practitioner or user of the instrument 10 to limit the inherent closing (positive) pressure applied by the end tips, where this clamp-limiting is useful both to set the smallest tip gap (for example for use in a grasping function) and to maintain the largest tip gap (for example for use in a separating function.)

The careful reader familiar with the necessary technologies for manufacturing instruments such as described herein will understand that many embodiments are possible for implementing the functional teachings of the present invention. As such, it will be well understood that the preferred and alternate embodiments of the presently taught apparatus and methods, as well as the many taught use cases, should be considered as exemplary, rather than as limitations to the present invention. While certain features of the invention have been illustrated and described herein, other modifications and changes will occur to those skilled in the art. It is, therefore, to be understood that the appended claims are intended to cover all such modifications and changes as fall within the true spirit of the invention.

The invention claimed is:

1. A medical instrument for use by a practitioner to insert a punctum plug having a longitudinal axis into a punctal opening of an eye of a patient, facilitating the treatment of dry eye using lacrimal occlusion, where the instrument further comprises:

two arms each extending along a longitudinal axis from a proximal base to a holding surface, wherein each arm comprises a proximal portion, a wide portion angled outwardly from the proximal portion, a narrow portion angled inwardly from the wide portion and a distal portion, where each of the proximal portions of the arms are joined forming the proximal base, where each of the wide portions together provide a grasping surface, where each of the narrow portions together comprise a crisscross configuration, where each of the distal portions together form the holding surface for engaging and disengaging the punctum plug, and where the medical instrument is biased to a closed configuration, and a dilator for dilating the punctal opening in preparation to receive the punctum plug, where the dilator comprises a proximal end attached to the proximal base and a distal end extending therefrom, and where the distal end of the dilator forms an apex that is lesser in diameter than the diameter of the punctal opening.

2. The instrument of claim 1 wherein the dilator is further adapted with a profile for use as a sizer-dilator.

3. The instrument of claim 2 wherein the profile of the sizer-dilator is further adapted to include markings indicative of plug sizes.

4. The instrument of claim 2 wherein:

the dilator is further adapted to be a detachable dilator and the sizer-dilator is further adapted to be a detachable sizer-dilator, and the base is further adapted to include means for accepting the detachable dilator or the detachable sizer-dilator.

5. The instrument of claim 1 wherein at least one distal portion used in forming the holding surface includes using a distal end shape selected from the group consisting of: Plain, Cilia, Grooved, Brown-Addison, Round, Tissue, Angled-tip, and Singley.

6. The instrument of claim 1 wherein either one or both of the distal portions are further adapted to individually include or collectively form a receptacle for use in maneuvering the plug.

7. The instrument of claim 1 wherein either one or both of the distal portions are further adapted to comprise a distal base and a detachable tip, where the distal base is permanently attached to the respective narrow portion, where the tip is attachable to and detachable from the respective distal base.

8. The instrument of claim 1 wherein at least one of the distal portions is further adapted to engage a detachable tip sleeve having a tip longitudinal axis and interior tip cavity running along the tip longitudinal axis, where the tip cavity of the detachable tip sleeve is sufficient for receiving some or all of the distal portion such that the tip sleeve substantially fits over the distal portion.

9. The instrument of claim 8 for use in a replaceable tip sleeve system, where the system further comprises:

at least one sleeve tray having a longitudinal axis, where the sleeve tray provides an exposed tray cavity running substantially along the longitudinal axis of the tray, where the exposed tray cavity includes (i) a top entrance, and (ii) a front entrance, where the top entrance (i) provides removal/replacement access to the tray cavity for an engaged configuration of the distal portion and the detachable tip sleeve, where removal/replacement access is accomplished in a direction of motion that is substantially perpendicular to the longitudinal axis of the sleeve tray, where the front entrance (ii) provides engagement/disengagement access to the tray cavity for a disengaged configuration of the distal portion and the detachable tip sleeve, and where engagement/disengagement access is accomplished in a direction of motion that is substantially parallel to the longitudinal axis of the sleeve tray.

10. The replaceable tip sleeve system of claim 9, where the system further comprises:
a sleeve box having a longitudinal axis, a front end and a back end, where the sleeve box holds or otherwise comprises one or more of the at least one sleeve trays, where the longitudinal axis of the sleeve box lies substantially parallel with the longitudinal axis of the one or more sleeve trays, where the height of the sleeve box at the front end comprising the front entrance is greater than the height of the sleeve box at the back end, where the back end is opposite to the front end with respect to the longitudinal axis of the sleeve box.

11. The replaceable tip sleeve system of claim 10 further comprising a rack, where the rack comprises two or more sleeve boxes.

12. The instrument of claim 1 that has been further adapted to include mechanical means for limiting a positive opening pressure applied by the practitioner to the grasping surface, where the mechanical means prevents the wide portions from coming into physical contact.

13. The instrument of claim 1 the that has been further adapted to include mechanical means for limiting a positive closing pressure of the instrument, where the mechanical means comprise screw type means, sliding wedge type means, rotating oblong wheel type means or pivoting ratchet arms type means.

14. The instrument of claim 1 further comprising:
a separator for limiting a positive opening pressure applied by the practitioner to the grasping surface, where the separator prevents the wide portions from coming into physical contact.

15. The instrument of claim 1 wherein the grasping surface is further adapted to comprise surface changes for increasing grip.

* * * * *